(12) United States Patent
Bawendi et al.

(10) Patent No.: US 9,078,920 B2
(45) Date of Patent: Jul. 14, 2015

(54) COMPACT NANOPARTICLES FOR BIOLOGICAL APPLICATIONS

(71) Applicant: Massachusetts Institute of Technology, Cambridge, MA (US)

(72) Inventors: Moungi G. Bawendi, Cambridge, MA (US); He Wei, Cambridge, MA (US); Numpon Insin, Sakon Nakhon (TH); Hee-Sun Han, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 13/716,109

(22) Filed: Dec. 15, 2012

(65) Prior Publication Data

US 2013/0184444 A1    Jul. 18, 2013

Related U.S. Application Data

(60) Provisional application No. 61/576,819, filed on Dec. 16, 2011.

(51) Int. Cl.
| | | |
|---|---|---|
| C07C 211/00 | (2006.01) | |
| A61K 49/18 | (2006.01) | |
| H01F 1/00 | (2006.01) | |
| A61K 47/48 | (2006.01) | |
| A61K 49/22 | (2006.01) | |
| B22F 1/00 | (2006.01) | |

(52) U.S. Cl.
CPC ....... *A61K 49/1833* (2013.01); *A61K 47/48861* (2013.01); *A61K 49/186* (2013.01); *A61K 49/1839* (2013.01); *A61K 49/1866* (2013.01); *A61K 49/222* (2013.01); *B22F 1/0062* (2013.01); *H01F 1/0054* (2013.01); *B22F 1/0018* (2013.01); *Y10T 428/2982* (2015.01)

(58) Field of Classification Search
None
See application file for complete search history.

(56) References Cited

U.S. PATENT DOCUMENTS

2011/0026189 A1    2/2011   Wei et al.
2011/0287341 A1   11/2011   Inoue et al.

OTHER PUBLICATIONS

International Search Report; mailed May 13, 2013; International Application No. PCT/US2012/059692.
Lee, S. W. et al., "High-power lithium batteries from functionalized carbon-nanotube electrodes," *Nature Nanotechnology*, vol. 5, No. 7, Jul. 1, 2010, pp. 531-537.
Lee, S. W. et al., "Nanostructured carbon-based electrodes: bridging the gap between thin-film lithium-ion batteries and electrochemical capacitors," *Energy & Environmental Science*, vol. 4, No. 6, Jan. 1, 2011, p. 1972.
Chew, S. Y. et al, "Flexible free-standing carbon nanotube films for model lithium-ion batteries," *Carbon*, vol. 47, No. 13, Nov. 1, 2009, pp. 2976-2983.
Ng, S. H. et al., "Single wall carbon nanotube paper as anode for lithium-ion battery," *Electrochimica Acta*, vol. 51, No. 1, Oct. 5, 2005, pp. 24-25.
Byon, H. R. et al., "Thin films of carbon nanotubes and chemically reduced graphenes for electrochemical micro-capacitors," *Carbon*, vol. 49, No. 2, Sep. 29, 2010, pp. 457-467.

(Continued)

*Primary Examiner* — Clinton Brooks
(74) *Attorney, Agent, or Firm* — Steptoe & Johnson LLP

(57) ABSTRACT

A water soluble nanoparticle can include a ligand of formula (I). The ligand can provide zwitterionic character and can provide water solubility, small hydrodynamic diameter, chemical stability, and the capability to modify the nanoparticle with additional functional moieties such as a small molecule, nucleic acid, or protein.

11 Claims, 8 Drawing Sheets

(56) References Cited

OTHER PUBLICATIONS

Xu, G. et al., "Binder-free activated carbon/carbon nanotube paper electrodes for use in supercapacitors," *Nano Research*, vol. 4, No. 9, Sep. 1, 2011, pp. 870-881.

Zhi-Qiang, N. et al., "Cross-Disciplinary Physics and Related Areas of Science and Technology; Fabrication and electrochemical properties of free-standing single-walled carbon nanotube film electrodes," *Chinese Physics*, vol. 20, No. 2, Feb. 4, 2011, p. 28101.

Lee, S. W. et al., "Self-standing positive electrodes of oxidized few-walled carbon nanotubes for light-weight and high-power lithium batteries," *Energy & Environmental Science*, vol. 5, No. 1, Jan. 1, 2012, p. 5437.

COMPACT NANOPARTICLES FOR BIOLOGICAL APPLICATIONS

PRIORITY CLAIM

This application claims priority to U.S. Provisional Application No. 61/576,819, filed Dec. 16, 2011, which is incorporated by reference in its entirety.

STATEMENT REGARDING FEDERALLY SPONSORED RESEARCH OR DEVELOPMENT

This invention was made with government support under Grant Nos. U54 CA151884 and R01 CA126642 awarded by the National Institutes of Health and under Grant No. CHE0714189 awarded by the National Science Foundation and under Contract No. W911NF-07-D-0004 awarded by the Army Research Office. The government has certain rights in the invention.

TECHNICAL FIELD

The present invention generally relates to compact nanoparticles for biological applications and methods of making and using them.

BACKGROUND

Inorganic nanoparticles, such as superparamagnetic iron oxide nanoparticles (SPIONs), have various potential biomedical applications, including imaging applications, magnetic resonance imaging (MRI), sensing, and drug delivery. Such applications require nanoparticles that are hydrophilic and biocompatible. Appropriate surface derivatization can provide inorganic nanoparticles with the necessary hydrophilicity. Preferably the nanoparticles remain stable in aqueous solution, have a low level of non-specific protein binding, and a small hydrodynamic diameter.

SUMMARY

Inorganic nanoparticles having a compact and zwitterionic ligand can exhibit good water solubility, small hydrodynamic diameters (HD), stability with respect to time, pH, and salinity, and a low level of non-specific protein binding. Furthermore, the nanoparticles can be functionalized with one or more functional moieties, thereby imparting the nanoparticles with desired characteristics such as a specific binding affinity for a target molecule or receptor, or optical characteristics such as a desired color or fluorescence.

In one aspect, a water soluble nanoparticle includes an inorganic nanoparticle and a ligand of formula (I) bound to a surface of the inorganic nanoparticle, wherein formula (I) is:

$$A-L^1-Z^1-L^2-Z^2 \quad (I)$$

wherein A can be a moiety having affinity for a surface of the nanoparticle; $L^1$ and $L^2$, independently, can be linker moieties; $Z^1$ can include a first charged or ionizable group and $Z^2$ can include a second charged or ionizable group; provided that when charged, the first charged or ionizable group and the second charged or ionizable group take on opposite charges.

The ligand can be of formula (II):

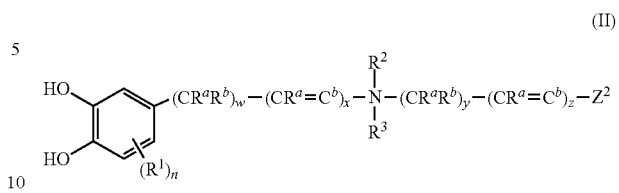

wherein $R^1$ can be halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

n can be 0, 1, 2, or 3;

each $R^a$ and each $R^b$, independently, can be hydrogen, hydroxy, halo, alkyl, alkoxy, alkenyl, alkynyl, cycloalkyl, cycloalkoxy, cycloalkenyl, aryl, heteroaryl, heterocyclyl or $NH_2$; wherein each of alkyl, alkoxy, alkenyl, cycloalkyl, cycloalkoxy, cycloalkenyl, aryl, heteroaryl, and heterocyclyl can be optionally substituted with 1 to 5 substituents independently selected from the group consisting of halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

each of w and y, independently, can be 0 to 8; each of x and z, independently, can be 0 to 4; provided that w and x are not simultaneously 0; and provided that y and z are not simultaneously 0;

$R^2$ can be $R^c$; and $R^3$ can be absent, or can be $R^c$;

each $R^c$, independently, can be hydrogen, alkyl, alkenyl, alkynyl, cycloalkyl, cycloalkenyl, aryl, heteroaryl, or heterocyclyl, wherein each of alkenyl, alkynyl, cycloalkyl, cycloalkenyl, aryl, heteroaryl, and heterocyclyl can be optionally substituted with 1 to 5 substituents independently selected from the group consisting of halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl; and $Z^2$ can be $—OH$, $—SH$, $—CO_2H$, $—OPO_3H_2$, $—PO_3H$, $—OSO_3H$, $—SO_3H$, or an ionized form thereof.

In some embodiments, w can be 2, 3, 4, 5, or 6; x can be zero; $R^2$ and $R^3$ can be each, independently, hydrogen or alkyl; y can be 2, 3, 4, 5, or 6; and z can be 0. $Z^2$ can be $—SO_3H$, or an ionized form thereof. The inorganic nanoparticle can include a superparamagnetic iron oxide nanoparticle. The nanoparticle can have a hydrodynamic diameter of 100 nm or less, 90 nm or less, 80 nm or less, 70 nm or less, 60 nm or less, 50 nm or less, 40 nm or less, 30 nm or less, 20 nm or less, or 10 nm or less.

The nanoparticle can further include a ligand of formula (III) bound to a surface of the inorganic nanoparticle, wherein formula (III) is:

$$A-L^1-L^2-H—R' \quad (III)$$

wherein A can be a moiety having affinity for a surface of the nanoparticle; $L^1$ and $L^2$, independently, can be linker moieties; H can be hydrophilic linker moiety, and R' can be a reactive group.

For the ligand of formula (III), A can be

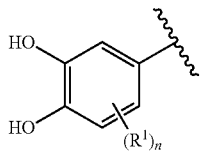

wherein $R^1$ can be halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl, and n is 0, 1, 2, or 3;

$L^1$ can be $-(CR^aR^b)_w-(CR^a=CR^b)_x-$, wherein w can be 0 to 8, x can be 0 to 4, provided that w and x can be not simultaneously 0;

$L^2$ can be $-C(O)-$, $-C(O)NR^c-$, $-O-$, $-OC(O)-$, $-OC(O)O-$, $-OC(O)NR^c-$, $-NR^c-$, $-NR^cC(O)-$, $-NR^cC(O)O-$, $-NR^cC(O)NR^c-$, or $-S-$;

H can be $-[(CR^aR^b)_aO]_k-[(CR^aR^b)_bO]_l-[(CR^aR^b)_cO]_m-$, wherein each of a, b, and c, independently, can be 2, 3, or 4, and each of k, l, and m, independently, can be 0 to 100;

each $R^a$ and each $R^b$, independently, can be hydrogen, hydroxy, halo, alkyl, alkoxy, alkenyl, alkynyl, cycloalkyl, cycloalkoxy, cycloalkenyl, aryl, heteroaryl, heterocyclyl or $NH_2$; wherein each of alkyl, alkoxy, alkenyl, cycloalkyl, cycloalkoxy, cycloalkenyl, aryl, heteroaryl, and heterocyclyl can be optionally substituted with 1 to 5 substituents independently selected from the group consisting of halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

each $R^c$, independently, can be hydrogen, alkyl, alkenyl, alkynyl, cycloalkyl, cycloalkenyl, aryl, heteroaryl, or heterocyclyl, wherein each of alkenyl, alkynyl, cycloalkyl, cycloalkenyl, aryl, heteroaryl, and heterocyclyl can be optionally substituted with 1 to 5 substituents independently selected from the group consisting of halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl; and R' can be $-CO_2H$, $-NH_2$, $-CH=CH2$, $-C\equiv CH$, $-N_3$, or $-SH$.

The nanoparticle can further include a ligand of formula (IV) bound to a surface of the inorganic nanoparticle, wherein formula (IV) is $$A-L^1-L^2-H-R-B \qquad (IV)$$

wherein A can be a moiety having affinity for a surface of the nanoparticle; $L^1$ and $L^2$, independently, can be linker moieties; H can be hydrophilic linker moiety; R can be a bond or a linker derived from R'; and B can be a functional moiety.

For the ligand of formula (IV), A can be

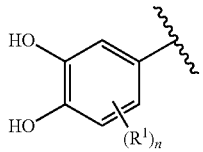

wherein $R^1$ can be halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl, and n can be 0, 1, 2, or 3;

$L^1$ can be $-(CR^aR^b)_w-(CR^a=CR^b)_x-$, wherein w can be 0 to 8, x can be 0 to 4, provided that w and x are not simultaneously 0;

$L^2$ can be $-C(O)-$, $-C(O)NR^c-$, $-O-$, $-OC(O)-$, $-OC(O)O-$, $-OC(O)NR^c-$, $-NR^c-$, $-NR^cC(O)-$, $-NR^cC(O)O-$, $-NR^cC(O)NR^c-$, or $-S-$;

H can be $-[(CR^aR^b)_aO]_k-[(CR^aR^b)_bO]_l-[(CR^aR^b)_cO]_m-$, wherein each of a, b, and c, independently, can be 2, 3, or 4, and each of k, l, and m, independently, can be 0 to 100;

each $R^a$ and each $R^b$, independently, can be hydrogen, hydroxy, halo, alkyl, alkoxy, alkenyl, alkynyl, cycloalkyl, cycloalkoxy, cycloalkenyl, aryl, heteroaryl, heterocyclyl or $NH_2$; wherein each of alkyl, alkoxy, alkenyl, cycloalkyl, cycloalkoxy, cycloalkenyl, aryl, heteroaryl, and heterocyclyl can be optionally substituted with 1 to 5 substituents independently selected from the group consisting of halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

each $R^c$, independently, can be hydrogen, alkyl, alkenyl, alkynyl, cycloalkyl, cycloalkenyl, aryl, heteroaryl, or heterocyclyl, wherein each of alkenyl, alkynyl, cycloalkyl, cycloalkenyl, aryl, heteroaryl, and heterocyclyl can be optionally substituted with 1 to 5 substituents independently selected from the group consisting of halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl; and R can be $-C(O)NH-$, $-NHC(O)-$, or $-S-$.

In some embodiments, B is a dye or a member of a binding pair.

The nanoparticle can further include a second, distinct ligand of formula (IV) bound to a surface of the inorganic nanoparticle.

In another aspect, method of making a water-soluble nanoparticle, includes providing an inorganic nanoparticle; and contacting the inorganic nanoparticle with a ligand of formula (I) bound to a surface of the inorganic nanoparticle, wherein formula (I) is:

$$A-L^1-Z^1-L^2-Z^2 \qquad (I)$$

wherein A can be a moiety having affinity for a surface of the nanoparticle; $L^1$ and $L^2$, independently, can be linker moieties; $Z^1$ can include a first charged or ionizable group and $Z^2$ can include a second charged or ionizable group; provided that when charged, the first charged or ionizable group and the second charged or ionizable group take on opposite charges.

The ligand can be of formula (II):

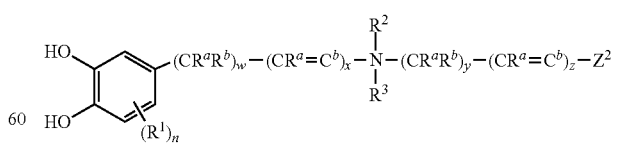

wherein $R^1$ can be halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

n can be 0, 1, 2, or 3;

each $R^a$ and each $R^b$, independently, can be hydrogen, hydroxy, halo, alkyl, alkoxy, alkenyl, alkynyl, cycloalkyl, cycloalkoxy, cycloalkenyl, aryl, heteroaryl, heterocyclyl or $NH_2$; wherein each of alkyl, alkoxy, alkenyl, cycloalkyl, cycloalkoxy, cycloalkenyl, aryl, heteroaryl, and heterocyclyl can be optionally substituted with 1 to 5 substituents independently selected from the group consisting of halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

each of w and y, independently, can be 0 to 8; each of x and z, independently, can be 0 to 4; provided that w and x are not simultaneously 0; and provided that y and z are not simultaneously 0;

$R^2$ can be $R^c$; and $R^3$ can be absent, or can be $R^c$;

each $R^c$, independently, can be hydrogen, alkyl, alkenyl, alkynyl, cycloalkyl, cycloalkenyl, aryl, heteroaryl, or heterocyclyl, wherein each of alkenyl, alkynyl, cycloalkyl, cycloalkenyl, aryl, heteroaryl, and heterocyclyl can be optionally substituted with 1 to 5 substituents independently selected from the group consisting of halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl; and $Z^2$ can be —OH, —SH, —$CO_2H$, —$OPO_3H_2$, —$PO_3H$, —$OSO_3H$, —$SO_3H$, or an ionized form thereof.

In some embodiments, w can be 2, 3, 4, 5, or 6; x can be zero; $R^2$ and $R^3$ can be each, independently, hydrogen or alkyl; y can be 2, 3, 4, 5, or 6; and z can be 0. $Z^2$ can be —$SO_3H$, or an ionized form thereof. The inorganic nanoparticle can include a superparamagnetic iron oxide nanoparticle.

Other aspects, embodiments, and features will become apparent from the following description, the drawings, and the claims.

DETAILED DESCRIPTION

Figure 1:
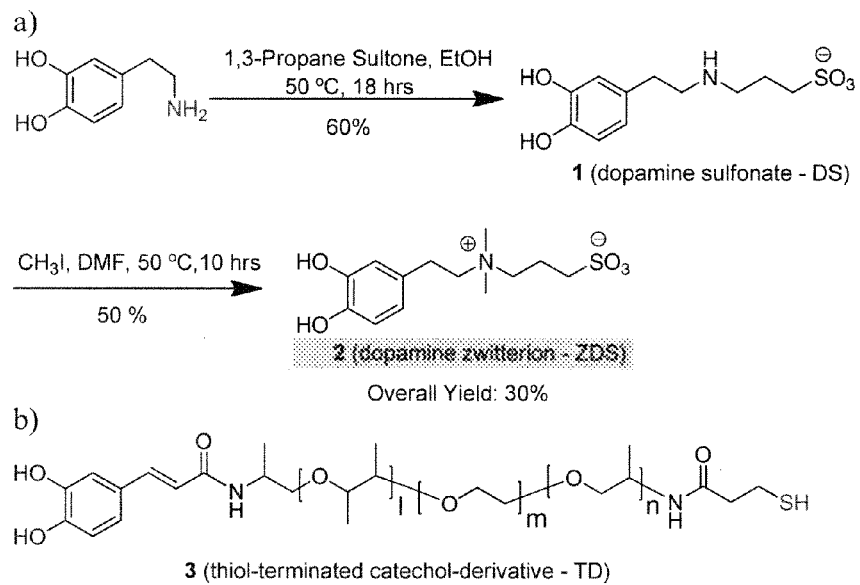
FIG. 1a shows the chemical structure and synthesis route of DS and ZDS ligand.
FIG. 1b shows the chemical structure of TD ligand.

Superparamagnetic iron oxide nanoparticles (SPIONs) have been used in-vitro and in-vivo as contrast agents to improve the sensitivity of magnetic resonance imaging (MRI). See, e.g., Park. Y.; et al., *J. Mater. Chem.* 2011, 21, 11472, which is incorporated by reference in its entirety. Relevant characteristics of SPIONs include a high saturation magnetic moment, chemical stability, and reduced toxicity compared to some other nanoparticle materials. Synthetic schemes for SPIONs having uniform size distributions generally involve the use of organic solvents and provide in SPIONs that are hydrophobic as synthesized.

Identifying ligands that render SPIONs hydrophilic and bio-compatible is important for demonstrating their potential uses in various biomedical applications. See, for example, (a) Na, H. B.; et al., *Adv. Mater.* 2009, 21, 2133; Latham A. H.; Williams, M. E. *Accounts of Chemical Research* 2008, 41, 411; and Jun, Y. W.; et al., *Angew. Chem. Int. Ed.* 2008, 47, 5122, each of which is incorporated by reference in its entirety. Dopamine can serve as a ligand to render SPIONs hydrophilic, due to strong interactions between vicinal diol groups and iron oxide as well as the hydrophilicity of amide and carboxyl groups (Xu C.; et al., *J. Am. Chem. Soc.* 2004, 126, 9938, which is incorporated by reference in its entirety).

Coupling polyethylene glycol (PEG) groups to dopamine derivatives can improve the stability and reduce the surface charge of water-soluble SPIONs, which in turn alleviates nonspecific binding to proteins (Amstad, E.; et al. *Nano Lett.* 2009, 9, 4042; Peng, S.; et al., *J. Am. Chem. Soc.* 2006, 128, 10676, each of which is incorporated by reference in its entirety). However, PEG-based ligands can significantly increase the effective hydrodynamic diameter (HD) of bio-compatible nanoparticles, which can restrict their access to confined spaces and prevent their renal elimination (Choi, H. S.; et al., *Nature Biotechnology* 2007, 25, 1165, which is incorporated by reference in its entirety). PEG-coated nanoparticle dispersions can also be unstable in high-salinity buffers, resulting in aggregation (see, e.g., Radziuk, D.; et al., *Macromol Rapid Comm* 2007, 28, 848, which is incorporated by reference in its entirety). There remains a need for novel ligands that have a strong binding affinity to inorganic nanoparticles, including SPIONs, yet minimize their effective HD while retaining high aqueous solubility, biocompatibility with minimal non-specific interactions, and long-term stability.

Small zwitterionic ligands for inorganic nanoparticles can provide bio-compatible nanoparticles with small HDs, a low level of non-specific interactions, and stability with respect to time, pH and salinity. In general, a ligand for a nanoparticle can include a moiety having affinity for a surface of the nanoparticle, one or more linker moieties; and two or more charged or ionizable groups that when in aqueous solution, under at least some conditions (e.g., at least some pH values), take on opposite charges. In some embodiments, the opposite charges are permanent charges. In other words, the ligand can bind to the nanoparticle and possess zwitterionic character. Preferably, the ligand can be small, such that the HD of the ligand-bound inorganic nanoparticle is not greatly increased over the diameter of the inorganic portion of the nanoparticle. In some cases, the ligand can have a molecular weight of 1,000 Da or less, 500 Da or less, 400 Da or less, 300 Da or less, or 200 Da or less.

A ligand for an inorganic nanoparticle can have formula (I):

wherein A is a moiety having affinity for a surface of the nanoparticle; $L^1$ and $L^2$, independently are linker moieties; $Z^1$ includes a first charged or ionizable group and $Z^2$ includes a second charged or ionizable group, provided that when charged, $Z^1$ and $Z^2$ take on opposite charges. In particular, when in aqueous solution, under at least some conditions (e.g., at least some pH values), the first and second charged or ionizable groups take on opposite charges, thereby imparting zwitterionic character.

A can be a monodentate, bidentate, tridentate, or polydentate moiety. A can include an o-dihydroxy aryl group (e.g., a catechol group), a carboxylate group, a phosphate group, or other group having affinity for a surface of the nanoparticle. An o-dihydroxy aryl group (e.g., a catechol group) can be particularly suitable for iron oxide nanoparticles.

Each of $L^1$ and $L^2$, independently, can be a bond; an alkylene group; an alkenylene group; an alkynylene group; a cycloalkylene group; a cycloalkenylene group; a heterocycloalkylene group; an arylene group; or a heteroarylene group. Each of $L^1$ and $L^2$, independently, can be optionally substituted with one or more halo, hydroxy, cyano, nitro, amino, carboxy, carboxyalkyl, alkyl, alkoxy, cycloalkyl, heterocycloalkyl, aryl, or heteroaryl groups. Each of $L^1$ and $L^2$, independently, can be optionally interrupted by one or more of —C(O)—, —C(O)NR$^c$, —O—, —OC(O)—, —OC(O)O—, —OC(O)NR$^c$—, —NR$^c$—, —NR$^c$C(O)—, —NR$^c$C(O)O—, —NR$^c$C(O)NR$^c$—, or —S—.

$Z^1$ includes a first charged or ionizable group. $Z^2$ includes a second charged or ionizable group. When in aqueous solution, under at least some conditions (e.g., at least some pH values), the first and second charged or ionizable groups take on opposite charges, thereby imparting zwitterionic character. Groups suitable for providing a positive charge include tertiary or quaternary amines. Groups suitable for providing a negative charge include alcohols, thiols, carboxylates, phosphates, phosphonates, sulfates, or sulfonates. In some embodiments, $Z^1$ is —NR$^2$—, —NR$^2$R$^3$— (i.e., a quaternary amine), or an ionized form thereof. In some embodiments, $Z^2$ is —OH, —SH, —CO$_2$H, —OPO$_3$H$_2$, —PO$_3$H, —OSO$_3$H, —SO$_3$H, or an ionized form thereof.

Each R$^c$, independently, is hydrogen, alkyl, alkenyl, alkynyl, cycloalkyl, cycloalkenyl, aryl, heteroaryl, or heterocyclyl, wherein each of alkenyl, alkynyl, cycloalkyl, cycloalkenyl, aryl, heteroaryl, and heterocyclyl are optionally substituted with 1 to 5 substituents independently selected from the group consisting of halo, oxo, CN, OH, NO$_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl.

A can be

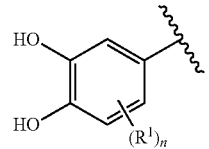

wherein R$^1$ is halo, oxo, CN, OH, NO$_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl, and n is 0, 1, 2, or 3.

$L^1$ can be —(CR$^a$R$^b$)$_w$—(CR$^a$=CR$^b$)$_x$—. $L^2$ can be —(CR$^a$R$^b$)$_y$—(CR$^a$=CR$^b$)$_z$—. Each of w and y, independently, can be 0 to 8; each of x and z, independently, can be 0 to 4; provided that w and x are not simultaneously 0, and provided that y and z are not simultaneously 0.

Each R$^a$ and each R$^b$, independently, is hydrogen, hydroxy, halo, alkyl, alkoxy, alkenyl, alkynyl, cycloalkyl, cycloalkoxy, cycloalkenyl, aryl, heteroaryl, heterocyclyl or NH$_2$; wherein each of alkyl, alkoxy, alkenyl, cycloalkyl, cycloalkoxy, cycloalkenyl, aryl, heteroaryl, and heterocyclyl are optionally substituted with 1 to 5 substituents independently selected from the group consisting of halo, oxo, CN, OH, NO$_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl.

In some embodiments, a ligand for an inorganic nanoparticle can have formula (II):

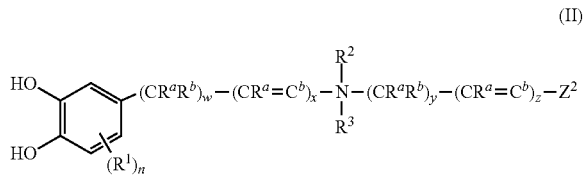

wherein R$^1$, R$^a$, R$^b$, n, w, x, y, and z, are defined as in formula (I) above, and $Z^2$ is —OH, —SH, —CO$_2$H, —OPO$_3$H$_2$, —PO$_3$H, —OSO$_3$H, —SO$_3$H, or an ionized form thereof.

R$^2$ is R$^c$; and R$^3$ is absent, or is R$^c$.

In some embodiments, w is 2, 3, 4, 5, or 6; x is zero; R$^2$ and R$^3$ are each, independently hydrogen or alkyl; y is 2, 3, 4, 5, or 6; z is 0; and $Z^2$ is —SO$_3$H, or an ionized form thereof.

An inorganic nanoparticle can have more than one type of ligand associated with it. For example, it can be desirable to provide a ligand that facilitates attachment of a variety of functional moieties to the nanoparticle.

A ligand for an inorganic nanoparticle can have formula (III):

where A is defined as in formula (I) above;
$L^1$ can be —(CR$^a$R$^b$)$_w$—(CR$^a$=CR$^b$)$_x$—
$L^2$ can be —C(O)—, —C(O)NR$^c$—, —O—, —OC(O)—, —OC(O)O—, —OC(O)NR$^c$—, —NR$^c$—, —NR$^c$C(O)—, —NR$^c$C(O)O—, —NR$^c$C(O)NR$^c$—, or —S—.
H is a hydrophilic linker moiety. H can be —[(CR$^a$R$^b$)$_a$O]$_k$—[(CR$^a$R$^b$)$_b$O]$_l$—[(CR$^a$R$^b$)$_c$O]$_m$—.
Each of a, b, and c, independently, is 2, 3, or 4. Each of k, l, and m, independently, is 0 to 100.
R$^a$, R$^b$, and R$^c$ are defined as in formula (I) above.

R' is a reactive group. R' can be, for example, —CO$_2$H, —NH$_2$, or —SH. Reactive group R' is capable of forming a covalent bond with a functional moiety to provide a ligand for an inorganic nanoparticle which can have formula (IV):

A-L$^1$-L$^2$-H—R—B        (IV)

where A, L$^1$ and L$^2$ are defined as in formula (I) above; H is a hydrophilic linking group; and R is a bond or a linker derived from R', and B is a functional moiety. R can be, for example, —C(O)NH—, —NHC(O)—, —S—, or another linker. B is a functional moiety such as a dye (e.g., a fluorescent dye) or a binding moiety, such as a small molecule, nucleic acid, peptide or protein that has a specific binding affinity for a corresponding member of a binding pair. The corresponding member can be a small molecule, nucleic acid, peptide or protein. Examples of binding pairs include biotin with avidin or streptavidin; nucleic acids having complementary sequences; antibodies with corresponding antigens; and receptor proteins with corresponding ligands.

An inorganic nanoparticle can include substantially crystalline inorganic material and can have a diameter in a range from about 1 nm to about 1000 nm. In this context, "substantially crystalline" is understood to mean that the inorganic nanoparticle comprises at least 50 volume percent and, preferably, at least 75 volume percent, crystalline material. In another embodiment, the inorganic nanoparticle is a single crystal. In one embodiment, the inorganic nanoparticle has a diameter in a range from about 1 nm to about 100 nm. In yet another embodiment, the inorganic nanoparticle has a diameter in a range from about 1 nm to about 10 nm.

The inorganic nanoparticle may include a variety of inorganic materials, including, but not limited to, metals in elemental form, transition metals, metal oxides, semiconductor materials, and superparamagnetic materials that are known in the art. For example, an inorganic nanoparticle comprising superparamagnetic material may include one of elemental iron, a spinel ferrite (Fe$_3$O$_4$), or at least one mixed spinel ferrite having the general formula MFe$_2$O$_4$, where M is a metal having an oxidation state other than exhibited by the predominant form that of iron, which is 3+. Non-limiting examples of M include iron (where a portion of the iron present iron is Fe$^{2+}$; i.e., iron having a 2+ oxidation state), copper, titanium, manganese, cobalt, nickel, chromium, gadolinium, zinc, yttrium, molybdenum, and vanadium.

In one particular embodiment, the inorganic nanoparticle is spherical and has a diameter in a range from about 1 nm to about 1000 nm. The inorganic nanoparticle may also be in another shape.

An outer coating can be disposed on an outer surface of inorganic nanoparticle such that the outer coating substantially covers and encloses the inorganic nanoparticle. The outer coating serves to stabilize the inorganic nanoparticle; i.e., the outer coating prevents the inorganic nanoparticle from contacting an adjacent inorganic nanoparticle, thereby preventing a plurality of such nanoparticles from agglomerating. Thus, the outer coating is sufficiently thick to stabilize the inorganic nanoparticle and prevent such contact.

The nanoparticle may be formed by a non-aqueous synthetic route for the formation of monodisperse crystalline nanoparticles, which is described in U.S. Patent Application Publication No. 2004/00229737 and in U.S. Pat. No. 6,797,380, each of which is incorporated by reference in its entirety. Organometallic precursor materials, such as, but not limited to, transition metal carbonyl compounds, are thermally decomposed in a solvent and in the presence of a surfactant and an oxidant. The organometallic precursors are provided in an appropriate stoichiometric ratio to a nonpolar aprotic solvent containing the surfactant and the oxidant.

A nonpolar aprotic organic solvent is combined with an oxidant and a first surfactant. The nonpolar aprotic solvent is thermally stable at the temperatures at which the plurality of nanoparticles are formed. In one embodiment, the nonpolar aprotic solvent has a boiling point in the range from about 275° C. to about 340° C. Suitable nonpolar aprotic solvents include, but are not limited to, dioctyl ether, hexadecane, trioctylamine, tetraethylene glycol dimethyl ether (also known as "tetraglyme"), and combinations thereof. The oxidant comprises at least one of an organo-tertiary amine oxide, a peroxide, an alkylhydroperoxide, a peroxyacid, molecular oxygen, nitrous oxide, and combinations thereof. In one embodiment, the oxidant comprises an organo-tertiary amine oxide having at least one methyl group. One non-limiting example of such an oxidant is trimethyl amine oxide.

The first surfactant optionally can include at least one of a polymerizable functionalized group, an initiating functionalized group, and a cross-linking functionalized group. An amount of the first surfactant is provided to the nonpolar aprotic organic solvent to produce a first concentration of the first surfactant in the nonpolar aprotic solvent. The polymerizable functionalized group may comprise at least one of an alkene, an alkyne, a vinyl (including acrylics and styrenics), an epoxide, an azeridine, a cyclic ether, a cyclic ester, and a cyclic amide. The initiating functionalized group may comprise at least one of a thermal or photoinitiator, such as, but not limited to, an azo compound, a hydroxide, a peroxide, an alkyl halide, an aryl halide, a halo ketone, a halo ester, a halo amide, a nitroxide, a thiocarbonyl, a thiol, an organo-cobalt compound, a ketone, and an amine. The cross-linking functionalized group may be one of a thiol, an aldehyde, a ketone, a hydroxide, an isocyanide, an alkyl halide, a carboxylate, a carboxylic acid, a phenol, an amine, and combinations thereof.

At least one organometallic compound is provided to the combined nonpolar aprotic organic solvent, oxidant, and first surfactant. The at least one organometallic compound comprises at least one metal and at least one ligand. The metal may comprise a transition metal, such as, but not limited to, iron, nickel, copper, titanium, cadmium, cobalt, chromium, manganese, vanadium, yttrium, zinc, and molybdenum, or other metals, such as gadolinium. The at least one ligand may comprise at least one of carbonyl group, a cyclo octadienyl group, an organophosphine group, a nitrosyl group, a cyclo pentadienyl group, a pentamethyl cyclo pentadienyl group, a π-acid ligand, a nitroxy group, and combinations thereof. Non-limiting examples of the at least one organometallic compound include iron carbonyl (Fe(CO)$_5$), cobalt carbonyl (Co(CO)$_8$), and manganese carbonyl (Mn$_2$(CO)$_{10}$). In one embodiment, an amount of the at least one organometallic compound is provided to the aprotic solvent such that a ratio of the concentration of the at least one organometallic compound to the concentration of the oxidant has a value in a range from about 1 to about 10.

In one embodiment, a first organometallic compound is provided to the combined nonpolar aprotic organic solvent, oxidant, and first surfactant. The combined first organometallic compound, nonpolar aprotic organic solvent, oxidant, and first surfactant are then preheated under an inert gas atmosphere to a temperature for a time interval. The preheating serves to remove the ligands from the metal cation in the first organometallic compound. In one embodiment, the combined first organometallic compound, nonpolar aprotic organic solvent, oxidant, and first surfactant are preheated to a temperature in a range from about 90° C. to about 140° C. for a time interval ranging from about 15 minutes to about 90 minutes.

In another embodiment, the combined nonpolar aprotic solvent, oxidant, first surfactant, and the at least one organometallic compound are heated to under an inert gas atmosphere to a first temperature and maintained at the first temperature for a first time interval. At this point, the at least one organometallic compound reacts with the oxidant in the presence of the first surfactant and the nonpolar aprotic solvent to form a plurality of nanoparticles, wherein each nanoparticle comprises a crystalline inorganic nanoparticle and at least one outer coating comprising the first surfactant, which is disposed on an outer surface of the inorganic nanoparticle and substantially covers and encloses the substantially crystalline inorganic nanoparticle.

The first temperature to which the combined nonpolar aprotic solvent, oxidant, first surfactant, and the at least one organometallic compound are heated is dependent upon the relative thermal stability of the at least one organometallic compound that is provided to the aprotic solvent. The first temperature is in a range from about 30° C. to about 400° C. In one embodiment, the first temperature is in a range from about 275° C. to about 400° C. and, preferably, in a range from about 275° C. to about 310° C. The length of the first time interval may be from about 30 minutes to about 2 hours, depending on the particular organometallic compounds and oxidants that are provided to the aprotic solvent.

In one embodiment, the method may further comprise the step of precipitating the plurality of nanoparticles from the nonpolar aprotic solvent. Precipitation of the plurality of nanoparticles may be accomplished by adding at least one of an alcohol or a ketone to the nonpolar aprotic solvent. Alcohols such as, but not limited to, methanol and ethanol may be used. Alcohols having at least three carbon atoms, such as isopropanol, are preferred, as their use tends to produce the smallest degree of agglomeration of the plurality of nanoparticles. Ketones such as, but not limited to, acetone may be used in conjunction with—or separate from—an alcohol in the precipitation step.

In another embodiment, the method may also further include a step in which a ligand either partially of completely replaces—or is exchanged for—the first surfactant in the outer coating. Following the formation of the plurality of nanoparticles, the nanoparticles are precipitated and resuspended in a liquid including a desired ligand (e.g., the neat ligand, or a solution of ligand in a solvent compatible with the existing outer coating). This procedure may be repeated as necessary. Alternatively, the ligand is added to the nonpolar aprotic solvent such that the ligand is present in a second concentration, the second concentration being greater than a first concentration of the first surfactant in the nonpolar aprotic solvent. The nanoparticles may be subjected to additional rounds of ligand exchange. For example, it may be desirable to exchange the surfactant for an intermediate ligand which is subsequently exchanged for the desired ligand. The desired ligand can include a ligand of any of formulas (I)-(IV), or a mixture thereof.

In one particular embodiment, a method of forming a plurality of monodisperse crystalline nanoparticles, wherein each of the plurality of monodisperse nanoparticles comprises a crystalline mixed spinel ferrite core and an outer coating disposed on an outer surface of the crystalline mixed spinel ferrite core. The crystalline mixed spinel ferrite core comprises iron in a first oxidation state and a transition metal in a second oxidation state, wherein the second oxidation state is different from the first oxidation state.

In this method, an oxidant and a first surfactant are combined a nonpolar aprotic organic solvent. In one embodiment, the nonpolar aprotic organic solvent has a boiling point in a range from about 275° C. to about 340° C. Suitable nonpolar aprotic solvents include, but are not limited to, dioctyl ether, hexadecane, trioctylamine, trioctylamine, tetraethylene glycol dimethyl ether (also known as "tetraglyme"), and combinations thereof. The oxidant comprises at least one of an organo-tertiary amine oxide, a peroxide, an alkylhydroperoxide, a peroxyacid, molecular oxygen, nitrous oxide, and combinations thereof. In one embodiment, the oxidant comprises an organo-tertiary amine oxide having at least one methyl group. One non-limiting example of such an oxidant is trimethyl amine oxide. The first surfactant optionally can include at least one of a polymerizable functionalized group, an initiating functionalized group, and a cross-linking functionalized group. An amount of the first surfactant is provided to the nonpolar aprotic organic solvent to produce a first concentration of the first surfactant in the nonpolar aprotic solvent. Suitable polymerizable functionalized groups, initiating functionalized groups, and cross-linking functionalized groups for the first surfactant are the same as those that have been previously described herein.

The combined nonpolar aprotic solvent, oxidant, and first surfactant can be heated under an inert gas atmosphere to a first temperature. In one embodiment, the first temperature is in a range from about 90° C. to about 140° C. An organo-iron compound is then provided to the combined nonpolar aprotic solvent, oxidant, and first surfactant at the first temperature. The organo-iron compound, together with the combined nonpolar aprotic solvent, oxidant, and first surfactant, is maintained at the first temperature for a first time interval under an inert gas atmosphere. The ligands are removed from the organo-iron compound in the presence of the oxidant; the first time interval must therefore be of sufficient duration to accomplish the removal. In one embodiment, the first time interval may be from about 15 minutes to about 90 minutes.

The organo-iron compound comprises iron and at least one ligand. In one embodiment, the at least one ligand comprises at least one of a carbonyl group, a cyclo octadienyl group, an organophosphine group, a nitrosyl group, a cyclo pentadienyl group, a pentamethyl cyclo pentadienyl group, π-acid ligand, a nitroxy group, and combinations thereof. One non-limiting example of the organo-iron compound is iron carbonyl (Fe$(CO)_5$).

Following the expiration of the first time interval, at least one organo-transition metal compound is added to and combined with the organo-iron compound and the combined nonpolar aprotic solvent, oxidant, and first surfactant together at the first temperature. The at least one organo-transition metal compound comprises a transition metal and at least one ligand. In one embodiment, the transition metal is one of iron, nickel, copper, titanium, cobalt, chromium, manganese, vanadium, yttrium, zinc, and molybdenum, and the at least one ligand comprises at least one of a carbonyl group, a cyclo octadienyl group, an organophosphine group, a nitrosyl group, a cyclo pentadienyl group, a pentamethyl cyclo pentadienyl group, a π-acid ligand, a nitroxy group, and combinations thereof. Analogous organo-metallic compounds of selected metals, such as gadolinium, maybe substituted for organo-transition metal compounds. Non-limiting examples of the at least one organo-transition metal compound include cobalt carbonyl ($Co(CO)_8$) and manganese carbonyl ($Mn_2(CO)_{10}$).

The at least one organo-transition metal compound, organo-iron compound, nonpolar aprotic solvent, oxidant, and first surfactant, combined together, are heated to a second temperature and maintained at the second temperature for a second time interval. The organo-iron compound reacts with the at least one organo-transition metal compound at the second temperature to form a plurality of monodisperse nanoparticles, wherein each of the plurality of monodisperse nanoparticles comprises a crystalline mixed spinel ferrite core and an outer coating comprising the first surfactant, disposed on an outer surface of the crystalline mixed spinel ferrite core. Iron carbonyl ($Fe(CO)_5$), for example, may react with cobalt carbonyl ($Co(CO)_8$) to form nanoparticles comprising the crystalline cobalt iron spinel ferrite $CoFe_2O_4$. Alternatively, iron carbonyl may react with manganese carbonyl ($Mn_2(CO)_{10}$) to form nanoparticles comprising the crystalline manganese iron spinel ferrite $MnFe_2O_4$. Where the at least one organo-transition metal compound comprises iron carbonyl, nanoparticles comprising the crystalline mixed γ-iron oxide/ferrite ($\gamma\text{-}Fe_2O_3)_{1-y}(Fe_3O_4)_y$ are formed.

In one embodiment, the second temperature is in a range from about 285° C. to about 400° C. In another embodiment, the second temperature is in a range from about 275° C. to about 310° C. In one embodiment, the second time interval may range from about 30 minutes to about two hours.

The plurality of nanoparticles can be precipitated from the nonpolar aprotic solvent by adding at least one of an alcohol or a ketone to the nonpolar aprotic solvent. Alcohols such as, but not limited to, methanol and ethanol may be used. Alcohols having at least three carbon atoms, such as isopropanol, are preferred, as their use tends to produce the smallest degree of agglomeration. Ketones such as, but not limited to, acetone may be used in conjunction with—or separate from—an alcohol in the precipitation step.

The plurality of nanoparticles produced by the methods described are monodisperse; i.e., the nanoparticles are substantially identical in size and shape.

Other methods are described in U.S. Pat. Nos. 6,962,685 and 7,128,891, each of which is incorporated by reference in its entirety, in which nanoparticles are made by treating a mixture of metal salt, alcohol, an acid and amine with ethanol to precipitate magnetic materials.

EXAMPLES

A compact and water-soluble zwitterionic ligand with strong binding affinity to SPIONs was designed and prepared. This ligand resulted in bio-compatible SPIONs with minimized HDs, minimal non-specific interactions, and stability with respect to time, pH and salinity.

A zwitterion dopamine sulfonate (ZDS) ligand was designed with the following considerations in mind: (1) the dopamine moiety provides strong coordination to the iron oxide surface, (2) the sulfonate group conveys high water solubility, and (3) the combination of a quaternary amine group and the sulfonate group provides the ligand with a zwitterionic character, enabling pH stability and minimizing non-specific interactions with proteins.

As shown in FIG. 1A, the ZDS ligand was synthesized from commercially available dopamine via a simple two step reaction: first, the sulfonation of dopamine was accomplished by ring opening of the 1,3-propane sultone, followed by methylation of the amino group by addition of iodomethane (supporting information). Hydrophobic SPIONs were synthesized from the thermal decomposition of $Fe(CO)_5$ in a dioctyl ether solvent in the presence of native oleic acid ligands and trimethylamine N-oxide oxidizing reagent. See, e.g., Woo, K.; et al., *Chem Mater* 2004, 16, 2814; Hyeon, T.; et al., *J Am Chem Soc* 2001, 123, 12798; and Insin, N.; et al., *ACS Nano* 2008, 2, 197; each of which is incorporated by reference in its entirety.

Water soluble SPIONs were obtained by a two step ligand exchange process. The native hydrophobic oleic acid ligand was first exchanged by 2-[2-(2-methoxyethoxy)ethoxy]acetic acid (MEAA) ligand in methanol. The purpose of this first exchange is to increase the solubility of the SPIONs in the solvent mixture used in the second step. Next, in a dimethylformamide/water mixed solvent, the MEAA ligand was replaced by ZDS, dopamine sulfonate (DS, Compound 1, FIG. 1a), or mixtures of ZDS with thiol-terminated catechol-derivative (TD, Compound 3, FIG. 1b) for bio-conjugations. The DS ligand was utilized as a control with a charge similar to other small but negatively charged ligands, such as 2,3-dimercaptosuccinic acid. See, for example, Lee, J. H.; et al., *Nature Medicine* 2007, 13, 95; and Yoon, T. J.; et al., *Angew Chem Int Edit* 2011, 50, 4663; each of which is incorporated by reference in its entirety.

Figure 2:
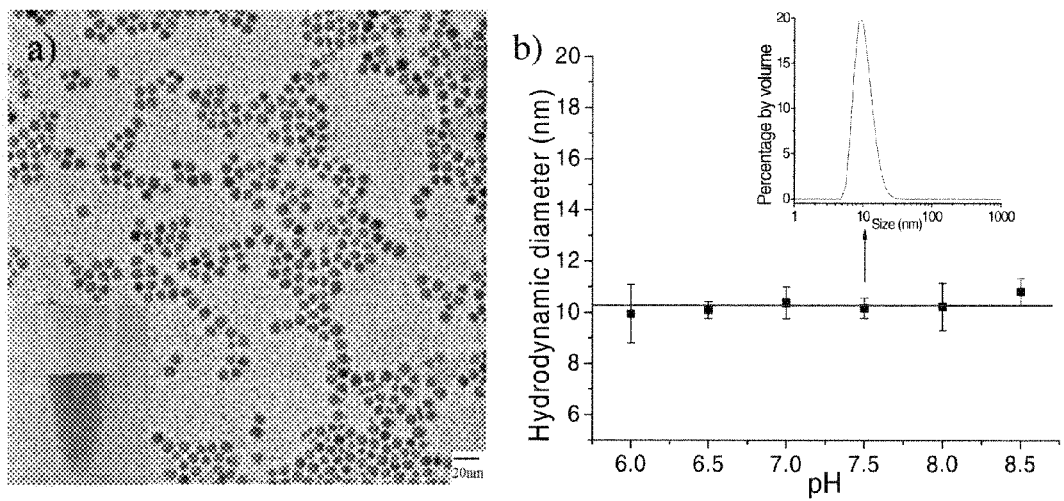
FIG. 2a shows TEM images of hydrophilic ZDS-NPs (Inset: photograph of ZDS-NPs dispersed in PBS 1×).
FIG. 2b shows hydrodynamic size of ZDS-NPs vs. pH (Inset: Size distribution of ZDS-NPs at pH=7.5).

The resulting water soluble ZDS ligand-exchanged SPIONs (ZDS-NPs) were stable and well dispersible at high NP concentrations in phosphate buffered saline (PBS 1×, inset of FIG. 2a). Transmission electron microscopy (TEM) further showed that the ZDS-NPs were nearly monodisperse in PBS 1× with an inorganic particle diameter of 8.0 nm (FIG. 2a). Moreover, dynamic light scattering (DLS) measurement revealed that the ZDS-NPs had a narrow size distribution (inset of FIG. 2b) with a hydrodynamic diameter (HD) of ~10 nm, indicating that the ZDS ligand contributes less than 1 nm to the overall radius. This size increment is significantly smaller than for dextran or PEG-coupled ligands, which can be on the order of 30 to 200 nm. See, e.g., Jung, C. W.; Jacobs, P. *Magn. Reson. Imaging* 1995, 13, 661; Wang, Y. X.; Hussain, S. M.; Krestin, G. P. *Eur. J. Radiol.* 2001, 11, 2319; and (a) Amstad, E.; Gillich, T.; Bilecka, I.; Textor, M.; Reimhult, E. *Nano Lett.* 2009, 9, 4042; each of which is incorporated by reference in its entirety. In addition, the HD of ZDS-NPs was insensitive to pH over the pH range of 6.0-8.5, indicating good colloidal stability over physiological pHs (FIG. 2b).

To study the in-vivo imaging potential of these NPs, a serum binding test was performed, which compared the sizes of NPs incubated with fetal bovine serum (FBS) and PBS 1×, respectively. Size-exclusion HPLC was used, with the retention times of NPs having an inverse relationship with the sizes of NPs. See Tromsdorf, U. I.; Bruns, O. T.; Salmen, S. C.; Beisiegel, U.; Weller, H. *Nano Lett* 2009, 9, 4434, which is incorporated by reference in its entirety.

Figure 3:
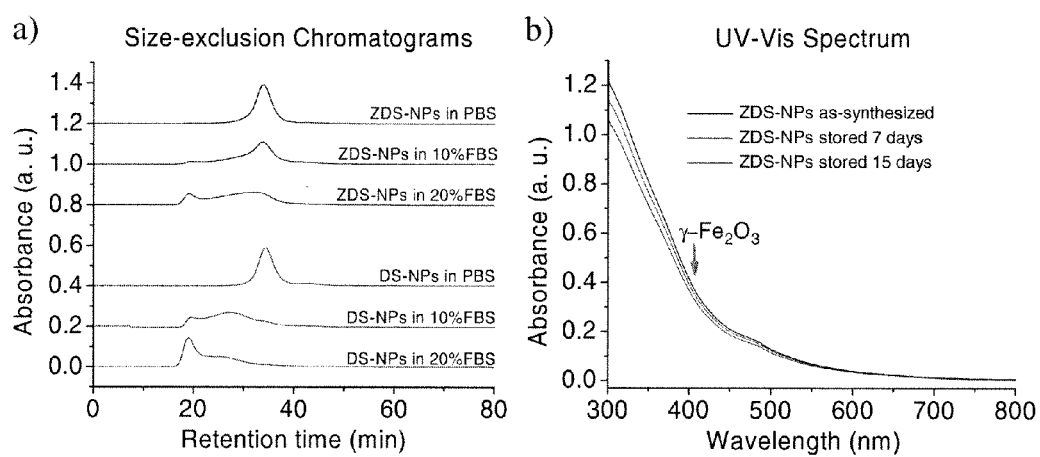
FIG. 3a shows chromatograms of SPIONs in serum binding test (absorbance vs. retention time).
FIG. 3b, UV-Vis spectrum of ZDS-NPs with the increase of storage time.

In PBS 1×, both DS-NPs and ZDS-NPs (FIG. 3a) were nearly monodisperse with a retention time of ~34 min. The size of DS-NPs after incubation with 10% FBS was larger than the size of DS-NPs after incubation with PBS 1×, showing a continuous distribution between 20 and 37 min; in contrast, the size distribution of ZDS-NPs after incubation of 10% FBS was similar to the size distribution of ZDS-NPs after incubation with PBS 1×. When the serum-to-NP ratio increased, DS-NPs after incubation with 20% FBS strongly aggregated and thus showed a retention time at ~18 min (corresponding to ~9 mL, approximately the void volume of the column; see Wong, C.; et al., *P Natl Acad Sci USA* 2011, 108, 2426, which is incorporated by reference in its entirety); in contrast, although a small portion of ZDS-NPs after incubation with 20% FBS showed a retention time at ~18 min (presumably caused by minor biological species of FBS that can bind to the nearly neutral ZDS-NPs; see Simberg, D.; et al., *Biomaterials* 2009, 30, 3926), most of the ZDS-NPs showed a continuous distribution between 20 and 37 min. These data indicated that the negatively charged DS-NPs had a high non-specific affinity towards serum proteins; particularly, DS-NPs showed a strong aggregation in 20% FBS. Therefore, although DS ligands also gave rise to water-soluble and small iron oxide NPs, the negative charge from the sulfonate group on the DS ligands electrostatically interacted with some of the proteins in FBS, and electrostatic interactions are thought to be important for the binding between iron oxide NPs and bovine serum albumin, a major component of FBS (see Yang, Q. Q.; Liang, J. G.; Han, H. Y. *J Phys Chem B* 2009, 113, 10454, which is incorporated by reference in its entirety).

In comparison with DS-NPs, ZDS-NPs showed a reduced non-specific affinity towards serum proteins. ZDS ligands not only provided good solubility and a small size to iron oxide NPs but also ensured their nearly neutral overall charge, which in turn decreased the non-specific interactions between NPs and serum proteins. These data therefore suggested that zwitterionic ZDS-NPs are more suitable than DS-NPs for in-vivo experiments and that their overall electrically neutral (e.g. zwitterionic) nature is important to their design. See, e.g., Liu, W. H.; Choi, H. S.; Zimmer, J. P.; Tanaka, E.; Frangioni, J. V.; Bawendi, M. *J Am Chem Soc* 2007, 129, 14530, which is incorporated by reference in its entirety.

The stability of NPs is also an important parameter for their biomedical applications. NPs were studied by measuring the UV-Vis absorption over extended periods of time. The UV-Vis absorbance curves (FIG. 3b), which reflects the concentration of SPIONs, were nearly identical over at least a 2 week period. Carpenter and coworkers proposed (Shultz, M. D.; Reveles, J. U.; Khanna, S, N.; Carpenter E. E. *J. Am. Chem. Soc.* 2007, 129, 2482, which is incorporated by reference in its entirety) that if SPIONs were only ligand exchanged by the simple dopamine molecule, rapid degradation of SPIONs may occur, thereby forming iron(III) oxyhydroxide. However, this phenomenon was not observed for either ZDS or DS coated SPIONs. In addition, ZDS-NPs were stable for at least one month in PBS 1× at 4° C. (within the error range of DLS measurements, all ZDS-NPs retained the same HD). In addition ZDS-NPs were soluble even in saturated NaCl solutions, a consequence of combining the strong o-dihydroxybenzene anchor group and the highly water-soluble sulfonate group. This is in contrast to PEG-coated or single charge-stabilized nanoparticles which aggregate in saturated NaCl solutions. See, for example, Radziuk, D.; Skirtach, A.; Sukhorukov, G.; Shchukin, D.; Mohwald, H. *Macromol Rapid Comm* 2007, 28, 848; and Bakandritsos, A.; Psarras, G. C.; Boukos, N. *Langmuir* 2008, 24, 11489, each of which is incorporated by reference in its entirety.

Iron oxide NPs were functionalized with streptavidin and fluorescent dyes for targeting and fluorescence imaging, respectively. In prior studies, long-chain ligands such as organic polymers were used for the water solubilization of iron oxide NPs (short-chain ligands were generally not hydrophilic enough), hence the hydrodynamic diameter (HD) of those biocompatible NPs was significantly larger than their inorganic diameter (see Boyer, C.; et al., *J Mater Chem* 2010, 20, 255; Eberbeck, D.; et al., *J Phys D Appl Phys* 2010, 43; Chen, H. W.; et al., *Biomaterials* 2010, 31, 5397, each of which is incorporated by reference in its entirety).

Figure 4:
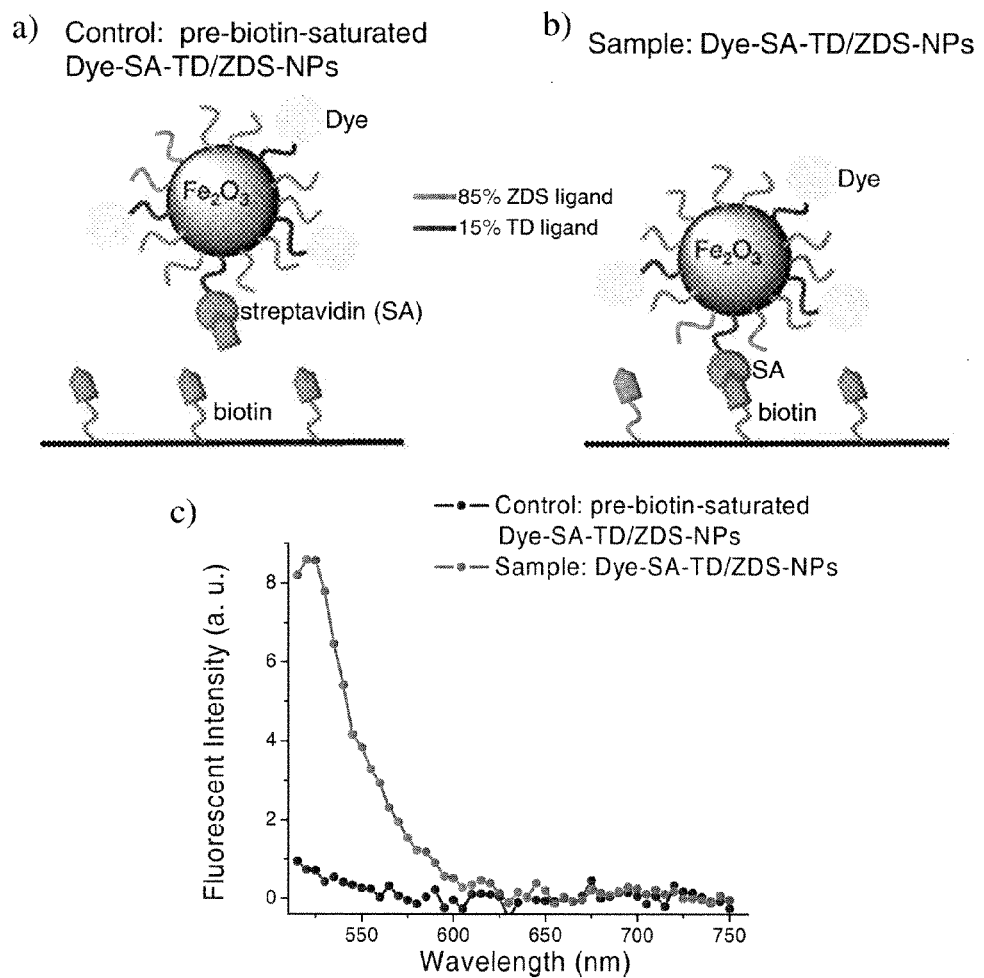
FIG. 4a shows a schematic diagram of the incubation of pre biotin-saturated Dye-SA-TD/ZDS-NPs in a biotin-plated well.
FIG. 4b shows a schematic diagram of the incubation of Dye-SA-TD/ZDS-NPs in a biotin-plated well.
FIG. 4c shows fluorescence spectra of both biotin-plated wells.

Here, a binary coating was designed, in which ZDS ligands provided water-solubility and short-chain ligands offered functionality. As shown in FIG. 1b, this short-chain ligand (TD ligand) included a catechol, a polyalkylene glycol, and a thiol. After ligand exchange with a mixture of 85% ZDS ligand and 15% TD ligand (mol %), the resulting TD/ZDS-NPs were conjugated by Alexa Fluor 488 maleimide dye (Dye, absorption peak=488 nm, emission peak=520 nm) and streptavidin-maleimide (SA) via a standard thiol-maleimide conjugation scheme. To demonstrate the functionalization of the TD/ZDS-NPs with streptavidin, biotin-coated wells on strip plate were incubated with either pre-biotin-saturated Dye-SA-TD/ZDS-NPs or Dye-SA-TD/ZDS-NPs (FIGS. 4a and 4b). Afterwards, the sample solutions were removed and the biotin-coated wells were rinsed with PBS. By measuring the resulting fluorescence of the wells, the signal intensity of Dye-SA-TD/ZDS-NPs was ~11 times higher than that of the pre-biotin-saturated Dye-SA-TD/ZDS-NPs (FIG. 4c). These data showed that the peptide-functionalized TD/ZDS-NPs may be appropriate for targeting cell receptors for specific labeling.

In conclusion, by using a compact zwitterionic dopamine sulfonate ligand coating on robust superparamagnetic iron oxide nanoparticles, aqueous iron oxide nanoparticles which are water-soluble, compact, and easily functionalized are prepared. Due to their zwitterionic nature, the ZDS-NPs have reduced nonspecific binding (compared to negatively charged SPIONs) to serum proteins; moreover, the streptavidin functionalized TD/ZDS-NPs labeled biotin specifically. These properties render the functionalized iron oxide nanoparticles suitable for in-vivo and in-vitro applications, where antibodies, peptides, or aptamers could be conjugated to TD/ZDS-NPs for targeting and imaging, and when combined with metal-binding proteins, TD/ZDS-NPs could serve as MRI-based metal ion sensors.

Experimental

Materials and Analysis

All chemicals unless indicated were obtained from Sigma Aldrich and used as received. Air-sensitive materials were handled in an Omni-Lab VAC glove box under dry nitrogen atmosphere with oxygen levels <0.2 ppm. All solvents were spectrophotometric grade and purchased from EMD Biosciences. TEM images of the iron oxide NPs were obtained with a JEOL 200CX electron microscope operated at 200 kV. NMR spectra were recorded on a Bruker DRX 400 NMR spectrometer. UV-Vis absorbance spectra were taken using a HP 8453 diode array spectrophotometer.

Synthesis of Iron Oxide NPs.

Maghemite ($Fe_2O_3$) magnetic NPs were prepared using a method modified from the literature. See Insin, N.; Tracy, J. B.; Lee, H.; Zimmer, J. P.; Westervelt, R. M.; Bawendi, M. G. *ACS Nano* 2008, 2, 197; and Woo, K.; Hong, J.; Choi, S.; Lee, H. W.; Ahn, J. P.; Kim, C. S.; Lee, S. W. *Chem. Mater.* 2004, 16, 2814; each of which is incorporated by reference in its entirety. As an example, for the synthesis of 8 nm NPs, 400 μL of $Fe(CO)_5$ was added to 0.75 mL of oleic acid in 20 mL of dioctyl ether at 100° C. The temperature was increased at a rate of 2° C./min to a final temperature of 290° C., at which it was held constant for 1 h. After the mixture was cooled to room temperature, 0.32 g of $(CH_3)_3NO$ was added as an oxidizing agent. See Hyeon, T.; Lee, S. S.; Park, J.; Chung, Y.; Bin Na, H. *J Am Chem Soc* 2001, 123, 12798, which is incorporated by reference in its entirety. The mixture was heated to 130° C. for 2 h and was then heated to 275° C. for 15 min. After cooling, the NPs were processed for storage by first adding ethanol to precipitate them. After centrifuging, the supernatant was discarded, and the NPs were then redispersed and stored in hexane. The typical concentration of iron oxide nanoparticles in hexane was ~2.8×10$^{-5}$ mol (of NPs)/L (24 g/L).

Synthesis of Dopamine Sulfonate.

Dopamine hydrochloride (1.1376 g, 6 mmol) was dissolved in 150 mL ethanol in a 500 mL round bottom flask. The flask was evacuated and back-filled with $N_2$, followed by slow addition of 28% ammonium hydroxide (416 µL, 3 mmol) and 1,3-propanesultone (799 mg, 6.5 mmol). The solution was heated to 50° C. and stirred for 18 hrs, resulting in the formation of white precipitates. The solvent mixture was filtered and the white precipitate was washed with ethanol three times. The residual white solid was dried under reduced pressure and characterized by NMR, which showed it to be pure (by NMR) dopamine sulfonate (DS). $^1$H NMR (400 MHz, $D_2O$): δ (ppm) 2.08 (m, 2H), 2.88-2.90 (m, 2H), 2.94-2.99 (m, 2H), 3.14-3.17 (m, 2H), 3.26 (m, 2H), 6.71-6.74 (m, 1H), 6.82-6.88 (m, 2H). $^{13}$C NMR (400 MHz, $D_2O$): δ (ppm) 21.11, 30.88, 46.11, 47.77, 48.57, 116.44, 121.06, 128.91, 143.01, 144.19.

Synthesis of Zwitterionic Dopamine Sulfonate.

Dopamine sulfonate (0.3286 g, 1 mmol) was dissolved in 150 mL dimethylformamide (DMF) in a 500 mL round bottom flask. Anhydrous sodium carbonate (0.2544 g, 2.4 mmol) was added into the DMF solution, although the sodium carbonate did not completely dissolve initially. The flask was evacuated and back-filled with $N_2$ three times, followed by the addition of iodomethane (2.2 mL, 35 mmol). The solution was stirred for 5-10 hrs at 50° C. (the sodium carbonate completely dissolved and the reaction mixture turned yellow upon completion of the methylation). The DMF was removed using a rotary evaporator at 40° C. and an oily mixture was obtained. 50 mL DMF/Ethyl acetate (1:10 v/v) was added to precipitate out a pale-yellow crude product. Following filtration, 50 mL DMF/Acetone (1:10 v/v) was added to the crude product and the mixture was refluxed at 55° C. for 2 hrs. The solution mixture was filtered again and the precipitate was collected. These reflux and filtration processes were repeated two more times and a white solid was obtained and characterized by NMR, which showed it to be pure (by NMR) zwitterionic dopamine sulfonate (ZDS). $^1$H NMR (400 MHz, $D_2O$): δ (ppm) 2.21 (m, 2H), 2.92-2.95 (m, 4H), 3.13 (s, 6H), 3.47-3.51 (m, 4H), 6.74-6.76 (m, 1H), 6.83-6.88 (m, 2H). $^{13}$C NMR (400 MHz, $D_2O$): δ (ppm) 18.12, 27.66, 47.10, 50.72, 62.02, 64.62, 116.49, 121.21, 128.23, 143.03, 144.18.

Ligand Exchange of Iron Oxide NPs.

Exchange of the native oleic acid surface ligands on NPs for the DS or ZDS ligand was carried out according to following procedures: To 25 µL of NPs in growth solution was added ethanol to the point of turbidity. Centrifugation and decantation yielded ~1 mg of dry pellet, to which 25 µL of neat 2-[2-(2-methoxyethoxy)ethoxy]acetic acid (MEAA) ligand and 75 µL of methanol were added. The mixture was stirred gently at 70° C. for 5 hrs and precipitated by adding 0.2 mL of acetone and 0.8 mL of hexane in succession. Centrifugation at 5800 rpm for 3 min yielded a clear supernatant, which was discarded. (Here the MEAA was used as an intermediate ligand to increase the solubility of NPs in 0.6 mL of DMF plus 0.3 mL of DI water, which was the solvent in the second ligand exchange process; this intermediate MEAA ligand is subsequently replaced by DS or ZDS later.) The pellet was then dispersed in 0.6 mL of DMF plus 0.3 mL of DI water, to which 50 mg of DS or ZDS ligand was added. Then the mixture was stirred again under $N_2$ at 70° C. for 12 hrs and precipitated by adding 5 mL of acetone. Centrifugation at 5800 RPM for 3 min yielded a clear supernatant, which was discarded. The pellet was then dispersed in 1 mL of phosphate buffer saline (PBS, pH=7.4: 1.5 mM $KH_2PO_4$, 4.3 mM $Na_2HPO_4$, 137 mM NaCl, 2.7 mM KCl) 1× and sonicated for 40 min. The sample was further purified using a dialysis filter (3 times) in order to thoroughly wash away excess ligand. DS or ZDS coated iron oxide nanoparticles could be dialyzed at least 10 times without noticeable aggregation, which is comparable to that of PEG-coupled nitrodopamine reported by Reimhult and co-workers. See Amstad, E.; Gillich, T.; Bilecka, I.; Textor, M.; Reimhult, E. *Nano Lett.* 2009, 9, 4042, which is incorporated by reference in its entirety. The ZDS coated iron oxide NPs could reach a concentration of more than ~$2 \times 10^{-5}$ mol/L (17 g/L).

Dynamic Light Scattering and pH Stability Measurements.

Light-scattering analysis was performed using a Malvern Instruments Nano-ZS90. While pHs varied from 6.0 to 8.5 with 0.5 spacing, all NP samples had the same concentration. Each autocorrelation function (ACF) was acquired for ~5 s, and averaged for ~10 min per measurement. Hydrodynamic diameters were obtained from a volume-weighted size distribution data analysis and reported as the average of triplicate measurements (error bars in FIG. 2b were the standard deviations of the values given by three parallel measurements).

Serum Binding Test.

ZDS coated iron oxide NPs (ZDS-NPs) and DS coated iron oxide NPs (DS-NPs) were washed by phosphate buffer containing $Mg^{2+}$ (pH=7: 1.5 mM $KH_2PO_4$, 4.3 mM $Na_2HPO_4$, 137 mM NaCl, 10 mM $MgCl_2$, 2.7 mM KCl) and plain PBS 1× in succession, followed by the filtration using 0.2 µm HT Tuffryn® membranes. The resulted ZDS-NPs and DS-NPs were incubated with 10% and 20% Fetal Bovine Serum (FBS) solution (in PBS 1×) as well as plain PBS 1×, respectively (see Zheng, M.; Davidson, F.; Huang, X. *J. Am. Chem. Soc.* 2003, 125, 7790, which is incorporated by reference in its entirety). Kept at room temperature for four hours, the six samples (ZDS-NPs with PBS, ZDS-NPs with 10% FBS, ZDS-NPs with 20% FBS, DS-NPs with PBS, DS-NPs with 10% FBS, DS-NPs with 20% FBS) were filtered by 0.2 µm HT Tuffryn® membranes before they were separately injected into a Superose™ 6 (GE Healthcare, 10/300 GL) size-exclusion column via a high-performance liquid chromatography machine manufactured by Agilent Technologies. With a flow rate of 0.5 mL PBS 1× per min, the iron oxide NPs were eluted and the absorption was monitored at 400 nm referencing to 600 nm and the resulted chromatograms were normalized by area.

Synthesis of Thiol-Terminated Catechol-Derivative and its Ligand Exchange.

Figure 5:
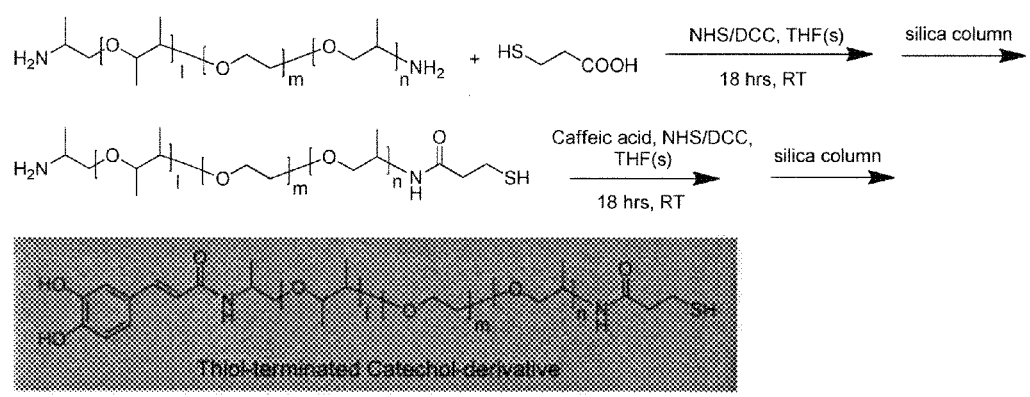
FIG. 5 shows the synthetic route to thiol-terminated catechol-derivative (TD) ligand.

The synthesis scheme is described in FIG. 5. 3-Mercaptopropionic acid (0.73 g, 6.9 mmol) was dissolved in 40 mL tetrahydrofuran (THF) in a 200 mL flask, followed by adding N-hydroxysuccinic anhydride (NHS, 1.03 g, 9.0 mmol) and N,N'-Dicyclohexylcarbodiimide (DCC, 1.84 g, 9.0 mmol). The solution was stirred at room temperature (RT) for 18 hrs, filtered, and the solvent removed using a rotary evaporator, yielding 3-mercaptopropionic NHS ester. 8.26 g (13.7 mmol) O,O'-Bis(2-aminopropyl)polypropylene glycol-block-polyethylene glycol-block-polypropylene glycol (Jeffamine® ED-600) was dissolved in 40 mL THF in a 200 mL flask, and the 3-mercaptopropionic NHS ester and triethyl amine (TEA, 0.77 g, 7.6 mmol) were slowly added into this solution. The resulting solution was also stirred at RT for 18 hrs, filtered, and the solvent removed using a rotary evaporator. The oily product was purified via a silica column with 20% MeOH/Dichloromethane (v/v) as the eluting solvent, yielding the thiol-terminated Jeffamine.

Separately, caffeic acid (1.25 g, 6.9 mmol) was dissolved in 80 mL THF in a 200 mL flask, followed by the addition of N-hydroxysuccinic anhydride (NHS, 1.03 g, 9.0 mmol) and N,N'-Dicyclohexylcarbodiimide (DCC, 1.84 g, 9.0 mmol). The solution was stirred at RT for 18 hrs, filtered, and the solvent removed using a rotary evaporator, yielding the caffeic NHS ester. Finally, the thiol-terminated Jeffamine was dissolved in 80 mL THF in a 200 mL flask, followed by adding the caffeic NHS ester and TEA (0.77 g, 7.6 mmol). This solution was stirred at RT for 18 hrs, filtered, and the solvent removed using a rotary evaporator. The crude product was again purified via a silica column using 20% MeOH/Dichloromethane (v/v) as the eluting solvent, yielding the thiol-terminated catechol-derivative. The presence of free thiol groups was confirmed by Ellman's test. The ligand exchange of TD/ZDS was done by using the same procedure in section "Ligand exchange of iron oxide NPs", except that 15% TD and 85% ZDS ligands (in molar ratio) were used yielding TD/ZDS coated iron oxide NPs (TD/ZDS-NPs).

Dye and Streptavidin Conjugation for Biotin Plate Test.

TD/ZDS-NPs were first treated with tris(2-carboxyethyl) phosphine to reduce any potential disulfide bonds, which may form during the ligand exchange, to free thiol groups. 0.1 mg Alexa Fluor 488 maleimide dye (purchased from Invitrogen) and 1 mg streptavidin-maleimide (SA) were reacted with 200 μL TD/ZDS-NPs at 37° C. for 4 hrs. When the reaction was finished, the excess dye and streptavidin were immediately removed by dialysis (3 times), yielding Dye-SA-TD/ZDS-NPs with a hydrodynamic diameter of ~17 nm. Then three samples were prepared: the first one was 100 μL plain PBS 1×, which was used as a blank; the second one was 100 μL Dye-SA-TD/ZDS-NPs in PBS 1× incubated with 50 μL biotin solution (80 mM in dimethyl sulfoxide) for 20 min, where SA should be saturated by biotin; the third one was 100 μL Dye-SA-TD/ZDS-NPs in PBS 1×. The three samples were then incubated in biotin-coated wells on a strip plate (purchased from Thermo Scientific, Reacti-Bind™ Biotin coated clear strip plate) for 20 min. The sample solutions were then removed and the biotin-coated wells were rinsed with PBS 1× three times and 100 μL PBS 1× was added to each well. The fluorescence profiles of these three wells were measured by Plate Reader Machine (BioTek, SYNERGY 4) with emission wavelength from 520 nm to 750 nm. Both the results of the second sample (pre-biotin-saturated Dye-SA-TD/ZDS-NPs) and the third sample (Dye-SA-TD/ZDS-NPs) were blanked with the first sample (PBS 1× only).

In other examples, the magnetic characterization of ZDS-coated SPIONs and their in vitro and in vivo performance relative to non-specific interactions with HeLa cells and in mice, respectively, are reported. ZDS-coated SPIONs retained the superparamagnetism and saturation magnetization ($M_s$) of as-synthesized hydrophobic SPIONs, with $M_s$=74 emu/g [Fe]. Moreover, ZDS-coated SPIONs showed only small non-specific uptake into HeLa cancer cells in vitro and low non-specific binding to serum proteins in vivo in mice.

Maghemite ($Fe_2O_3$) magnetic NPs were prepared using a method modified from the literature. See, for example, Insin, N.; Tracy, J. B.; Lee, H.; Zimmer, J. P.; Westervelt, R. M.; Bawendi, M. G. *ACS Nano* 2008, 2, 197, which is incorporated by reference in its entirety. As an example, for the synthesis of 6 nm NPs, 400 μL of Fe(CO)$_5$ was added to 1.91 mL of oleic acid (≥99% by GC) in the mixture of 5.7 mL 1-octadecene and 14.3 mL 1-hexadecene at 100° C. The temperature was increased at a rate of 2° C./min to a final temperature of 290° C., at which it was held constant for 1 hr. After the mixture was cooled to room temperature, 0.32 g of $(CH_3)_3NO$ was added as an oxidizing agent. See, for example, Woo, K.; Hong, J.; Choi, S.; Lee, H. W.; Ahn, J. P.; Kim, C. S.; Lee, S. W. *Chem. Mater.* 2004, 16, 2814, which is incorporated by reference in its entirety. The mixture was heated to 130° C. for 2 hrs and was then quickly heated to 275° C. for 15 min. After cooling, adding ethanol, and centrifuging, the supernatant was discarded, and the precipitated NPs were then redispersed and stored in hexane.

NP Ligands.

Zwitterionic dopamine sulfonate (ZDS, MW: ~300 g/mol) and thiol-terminated catechol-derivative (TD, MW: ~850 g/mol) ligands were synthesized according to the protocol in the supporting information in, for example, Wei, H.; Insin, N.; Lee, J.; Han, H. S.; Cordero, J. M.; Liu, W. H.; Bawendi, M. G. *Nano Lett.* 2012, 12, 22, which is incorporated by reference in its entirety. Dextran (Dex) ligands (MW: ~6000 g/mol) were obtained from Sigma Aldrich. 1,2-dioleoyl-sn-glycero-3-phosphoethanolamine-N-[methoxy(polyethylene glycol)-2000] ammonium salt (PEG-lipid, MW: ~2800 g/mol) in chloroform solution was purchased from Avanti Polar Lipids.

Ligand Exchange of Iron Oxide NPs.

ZDS-coated iron oxide NPs (ZDS) and TD/ZDS-coated iron oxide NPs (TD/ZDS-NPs) were prepared according to the protocol in the supporting information of Wei, H.; Insin, N.; Lee, J.; Han, H. S.; Cordero, J. M.; Liu, W. H.; Bawendi, M. G. *Nano Lett.* 2012, 12, 22, which is incorporated by reference in its entirety. For the preparation of dextran-coated iron oxide NPs (Dex-NPs), ethanol was added into 25 μL of NPs in hexane stock solution up to the point of turbidity, ~1 mg of dry pellet was obtained by the followed centrifugation and decantation. Then 2-[2-(2-methoxyethoxy)ethoxy]acetic acid (MEAA) coated iron oxide NPs (MEAA-NPs) were prepared according to protocol in the Supporting Information of Wei, H.; Insin, N.; Lee, J.; Han, H. S.; Cordero, J. M.; Liu, W. H.; Bawendi, M. G. *Nano Lett.* 2012, 12, 22, which is incorporated by reference in its entirety. In 0.6 mL of DMF plus 0.3 mL of DI water, the as-synthesized MEAA-NPs pellet was dispersed and 50 mg dextran ligand was added. Then the mixture was stirred at 70° C. for 8 hrs and precipitated by adding 5 mL of acetone. Centrifugation at 5800 RPM for 3 min yielded a clear supernatant, which was discarded. The pellet was then dispersed in 1 mL of phosphate buffer saline (PBS) 1× and sonicated (Branson 3510) for 20 min. The sample was further purified using a dialysis filter (NMWL=50 kDa, 1 time) in order to wash away excess dextran ligand.

Dynamic Light Scattering and pH Stability Measurements.

Light-scattering analysis was performed using a Malvern Instruments Nano-ZS90. pH was varied from 6.0 to 8.5 with 0.5 increments with all NP samples at the same concentration. Each autocorrelation function (ACF) was acquired for ~10 s, and averaged for ~2 min per measurement. Hydrodynamic diameters were obtained from a volume-weighted size distribution data analysis and reported as the average of ten measurements (error bars in FIG. 1c were the standard deviations of the values given by the ten parallel measurements).

Encapsulation of Iron Oxide NPs into PEG-Lipid Micelles.

Ethanol was added into 25 μL of NPs in hexane stock solution up to the point of turbidity. Centrifugation and decantation yielded ~1 mg of dry pellet, to which 0.5 mL of chloroform and 375 μL of PEG-lipid in chloroform (25 mg/mL) were added. Vortexing at 2000 RPM for 1 min yielded a homogeneous solution, which was dried in vacuo. The pellet was then dispersed in 2 mL PBS 1× and ultrasonicated (Microson ultrasonic cell disruptor) for 5 min. The sample was further purified using a dialysis filter (NMWL=50 kDa, 1 time).

Iron Determination.

Iron standards (1000 μg/mL, Ultra Scientific) were separately diluted to 2 μg/mL, 1.6 μg/mL, 0.8 μg/mL, 0.4 μg/mL, 0.2 μg/mL, and 0.04 μg/mL by using volumetric flasks. The above standards and blank (DI water) were transferred into a 96-well plate. Acetate buffer (2 mol/L, pH=4.8, with 10% ascorbic acid) and bathophenanthroline (BPT) were then added in succession. Pink-red color, from the formation of BPT-iron complex, gradually developed and was allowed to saturate before the absorbance of each well was measured at 540 nm by a plate reader (BioTek, SYNERGY 4). A calibration curve (FIG. 2d) was determined from the average of three parallel measurements yielding the linear fit Abs=0.05178+ 0.2887*$C_{Fe}$ ($R^2$=0.998), where Abs is the absorbance at 540 nm and $C_{Fe}$ is the iron concentration in μg/mL. Hydrophobic NPs, MEAA-coated NPs, and TD/ZDS-NPs were dried in vacuo and then digested by 6 mol/L hydrochloric acid. Iron determination of NPs followed the same protocol as that of iron standards and the results were averaged from three parallel measurements.

Cellular Uptake into HeLa Cells.

HeLa cells were obtained from American Type Culture Association. The cells were cultured in full medium (DMEM medium supplemented with 10% fetal bovine serum and 100 IU/mL penicillin-streptomycin). The cell density was determined using a hemocytometer prior to any experiments. After which, approximately 10 million cells were washed in full medium, centrifuged at 1000 RPM for 5 min, and then redispersed in 10 mL pre-warmed full medium. For each assay, freshly prepared HeLa cell suspensions were used with a density ~$10^6$ cells per mL. A BD Falcon 12-well transparent assay plate (Fisher Scientific, Pittsburgh, Pa.) was utilized with an 18 mm pre-sterilized glass slide in each well. An aliquot of 800 μL pre-warmed full medium was added to each well. Afterwards, 200 μL of the HeLa cell suspension (approximately 0.2 million cells) was added to each well. The 12-well transparent assay plate was then incubated at 37° C. for 5 min, followed by the addition of 1000 μL iron oxide NP in full medium solution with specified concentrations. The iron oxide NP solution was then mixed gently with the cell suspension by pipet tips before the cells were cultured in a cell incubator for 24 hrs (37° C., 5% $CO_2$). Each well of HeLa cells was washed using 1 mL PBS 1× three times and then fixed at room temperature for 30 min using 1 mL 2% paraformaldehyde. A Prussian blue iron-staining solution was freshly prepared by mixing equal volume of 2% hydrochloric acid aqueous solution and 2% potassium ferrocyanide (II) trihydrate. The intracellular iron content of the fixed HeLa cells was stained by incubation with 1 mL Prussian blue iron-staining solution at 37° C. for 30 min before the cells were washed with 1 mL PBS 1× (twice). The micro cover glass slips bearing HeLa cells were mounted onto microscope slides separately, dried at room temperature, and finally imaged by a Carl Zeiss microscope. A slightly blue background was shown in FIG. 3a, presumably caused by the small amount of residual Fe-containing salts which can form from $FeCl_3$ in the cell media.

In Vivo Stability Test.

Male FVB mice were purchased from Charles River Laboratories International, Inc. and housed in an AAALAC-accredited facility in the Division of Comparative Medicine at MIT. All mice were studied according to an approved institutional protocol. Mice were anesthetized by intraperitoneal injection of a mixture of Ketamine and Xylazine. For in vivo NP stability tests, different NPs in PBS 1× solution were injected through the tail vein. After 10 min, blood was taken by cardiac puncture. For serum formation, the blood was left for 15 min at room temperature to coagulate, followed by centrifugation at 3000 RPM for 6 min. The supernatants (i.e. serums) were collected and further centrifuged at 13000 RPM for 10 min before they were separately injected into a Superose™ 6 (GE Healthcare, 10/300 GL) size-exclusion column via a gel-filtration chromatography machine (Amersham Biosciences, AKTAprime plus). With a flow rate of 0.5 mL/min PBS 1×, the serums were eluted and their fractions were collected at 1 min intervals within the retention time from 15 min to 53 min. To each fraction (0.5 mL), 50 μL of concentrated hydrochloric acid (~12 mol/L) was added, and the mixture was incubated at 60° C. for half an hour in order to digest iron oxide NPs. Centrifugation at 13000 RPM for 10 min yielded a clear supernatant, which was collected (white precipitates, presumably acidified serum proteins, were discarded). In order to determine the iron concentration of each fraction, 100 μL of the supernatant was transferred to a 96-well plate, where 100 μL of acetate buffer (2 mol/L, pH=4.8) and 50 μL of bathophenanthroline (BPT) were then added in succession. After the pink-red color developed and saturated, the absorbance of each well was measured by a plate reader (BioTek, SYNERGY 4) at 540 nm. The small iron concentration peak of serum from control mouse in FIG. 4b is presumably caused by iron-containing proteins in the mouse serum.

Figure 6:
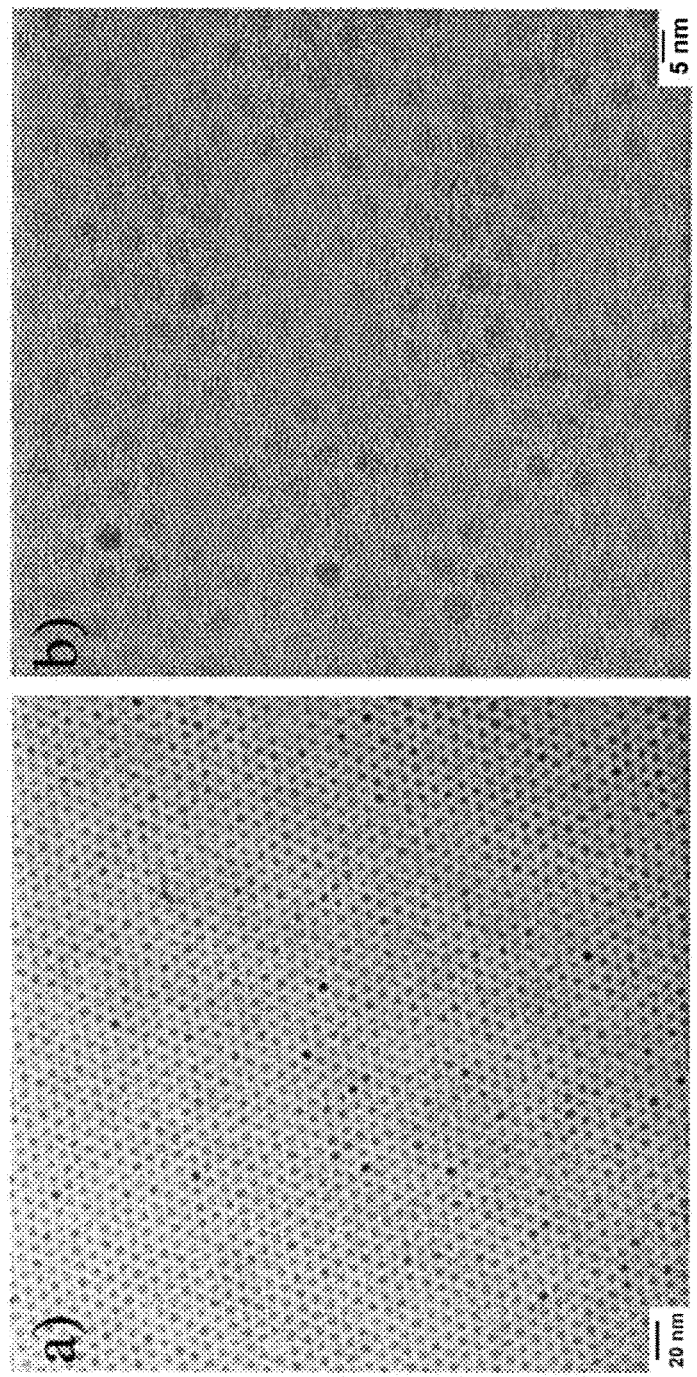
FIGS. 6a and 6b show a) TEM and b) HR-TEM images of as-synthesized hydrophobic NPs.

Hydrophobic iron oxide NPs were synthesized from the thermal decomposition of $Fe(CO)_5$ in a mixture of 1-octadecene (ODE) and 1-hexadecene (HDE) solvent in the presence of native oleic acid ligands and trimethylamine N-oxide oxidizing reagent. See, for example, Hyeon, T.; Lee, S. S.; Park, J.; Chung, Y.; Bin Na, H. *J. Am. Chem. Soc.* 2001, 123, 12798, and Woo, K.; Hong, J.; Choi, S.; Lee, H. W.; Ahn, J. P.; Kim, C. S.; Lee, S. W. *Chem. Mater.* 2004, 16, 2814, each of which have been incorporated by reference in its entirety. Different sizes of monodisperse NPs can be produced by adjusting the solvent boiling point, keeping both the concentration of $Fe(CO)_5$ and oleic acid constant as well as the growth time. See, for example, Schladt, T. D.; Graf, T.; Tremel, W. *Chem. Mater.* 2009, 21, 3183, which is incorporated by reference in its entirety. Changing the boiling point is achieved by changing the volume ratio of ODE to HDE. For the NPs used in this study, a 2:5 (by volume) mixture of ODE:HDE was used. Transmission electron microscopy (TEM) shows that the NPs are monodisperse (FIG. 6a) with an inorganic particle diameter of 5.3±0.3 nm (FIG. 6b). After the NPs were ligand-exchanged from oleic acid to zwitterionic dopamine sulfonate (ZDS), dynamic light scattering (DLS) measurement reveals that the ZDS-coated iron oxide NPs (ZDS-NPs) in aqueous buffer saline have a narrow size distribution with a hydrodynamic diameter (HD) of ~9.5 nm at pH=7.5, indicating that the ZDS ligand contributes ~2 nm to the overall radius. Moreover, the HD of ZDS-NPs is insensitive to pH ranging from 6.0 to 8.5, indicating good colloidal stability over physiological pHs. The size change induced by the ZDS ligand and the pH stability is consistent with the results described above; when combined with the recent advance in the synthesis of uniform and extremely small-sized iron oxide nanoparticles (see, for example, Kim, B. H.; Lee, N.; Kim, H.; An, K.; Park, Y. I.; Choi, Y.; Shin, K.; Lee, Y.; Kwon, S. G.; Na, H. B.; Park, J. G.; Ahn, T. Y.; Kim, Y. W.; Moon, W. K.; Choi, S. H.; Hyeon, T. *J. Am. Chem. Soc.* 2011, 133, 12624, which is incorporated by reference in its entirety), ZDS-coated iron oxide NPs would have the potentials to meet the requirement of HD for renal elimination. See, for example, Choi, H. S.; Liu, W.; Misra, P.; Tanaka, E.; Zimmer, J. P.; Kandapallil, B.; Bawendi, M. G.; Frangioni, J. V. *Nat. Biotechnol.* 2007, 25, 1165, which is incorporated by reference in its entirety. Moreover, for imaging and sensing purposes, it is also desirable to minimize the thickness of ligand shell in order that magnetic resonance signals from the inorganic core of iron oxide NPs can be maximized under the same hydrodynamic diameter, which is usually determined by the size limits for successful penetration and targeting in confined spaces. See, for example, Howarth, M.; Takao, K.; Hayashi, Y.; Ting, A. Y. *Proc. Natl. Acad. Sci. U.S.A.* 2005, 102, 7583, which is incorporated by reference by its entirety.

Figure 7:
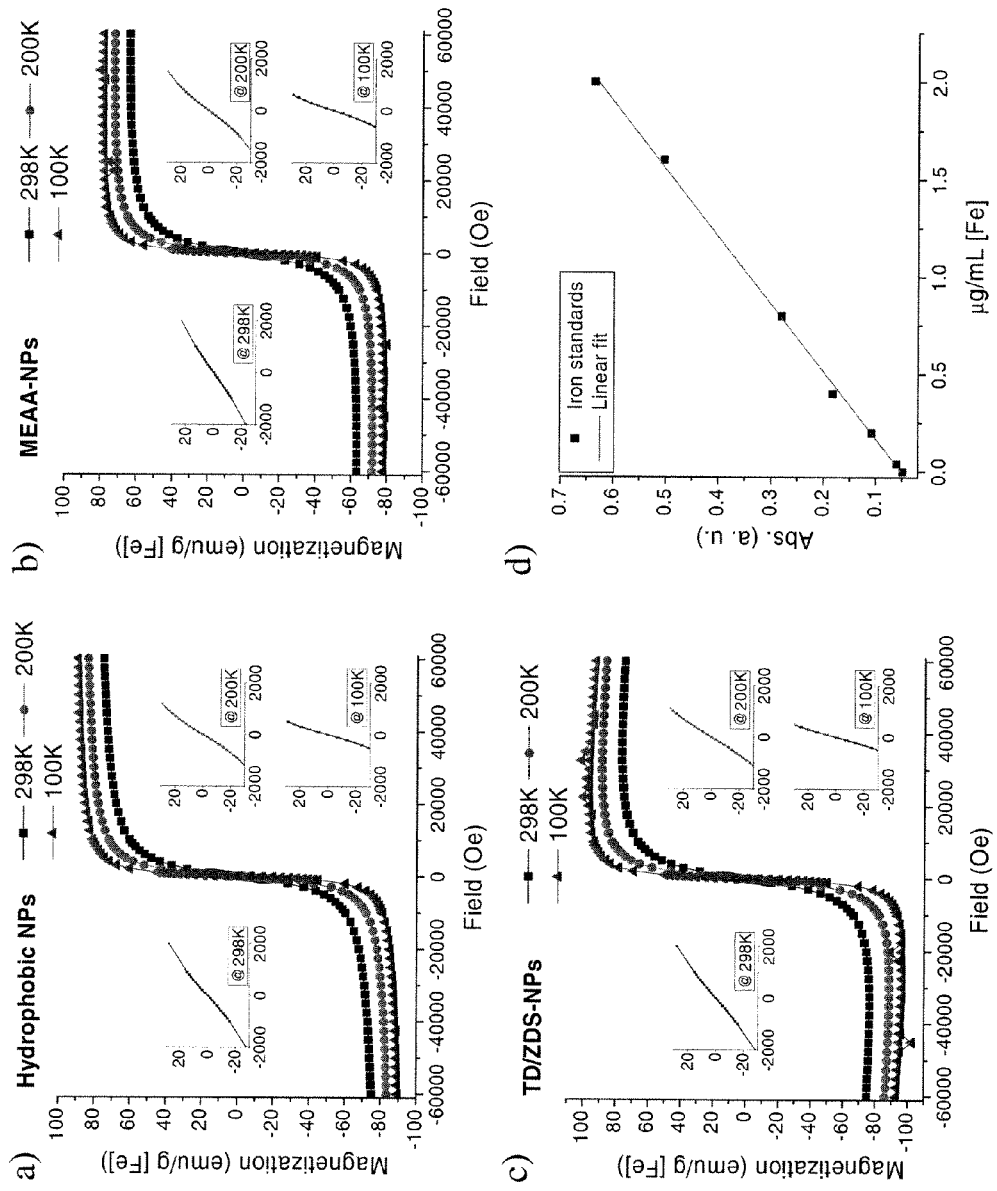
FIGS. 7a, 7b, 7c and 7d show SQUID curves of a) hydrophobic NPs, b) MEAA-NPs, and c) TD/ZDS-NPs (inset: magnified SQUID curves near zero field); d) Calibration curve of iron determination.

In order to characterize the magnetic behavior and saturation magnetization of as-synthesized SPIONs, the SQUID curves of hydrophobic NPs were measured at four different temperatures with the magnetic field ranging from −6 to 6 T. See, for example, Chertok, B.; Moffat, B. A.; David, A. E.; Yu, F. Q.; Bergemann, C.; Ross, B. D.; Yang, V. C. *Biomaterials* 2008, 29, 487, which is incorporated by reference in its entirety. After determining the mass of iron in the hydrophobic NPs (described above), the saturation magnetization ($M_s$) of hydrophobic NPs at room temperature was found to be ~74 emu/g [Fe] (FIG. 7a), which compares reasonably well with the bulk value for maghemite of 106 emu/g [Fe] (i.e. 74 emu/g [$Fe_2O_3$]). See, for example, Serna, C. J.; Morales, M. P. *Surface and Colloid Science* 2004, 17, 27, which is incorporated by reference in its entirety. Moreover, the inset of FIG. 7a shows that there are no hysteresis loops at zero field for hydrophobic NPs measured at 298 K, 200 K, or 100 K, indicating that the hydrophobic NPs are superparamagnetic at these temperatures. See, for example, Lin, C. R.; Chiang, R. K.; Wang, J. S.; Sung, T. W. *J. Appl. Phys.* 2006, 99; and Zhang, D. J.; Klabunde, K. J.; Sorensen, C. M.; Hadjipanayis, G. C. *Phys. Rev. B* 1998, 58, 14167, which is incorporated by reference in its entirety. In contrast, for hydrophobic NPs measured at 5 K, a hysteresis loop is observed. This is consistent with the blocking temperature of maghemite NPs, which is ~30 K for 5.5 nm maghemite NPs. See, for example, Martinez-Perez, M. J.; de Miguel, R.; Carbonera, C.; Martinez-Julvez, M.; Lostao, A.; Piquer, C.; Gomez-Moreno, C.; Bartolome, J.; Luis, F. *Nanotechnology* 2010, 21, which is incorporated by reference in its entirety. To further study the influence of ligand exchange and purification processes on M SQUID measurements on 2-[2-(2-methoxyethoxy)ethoxy] acetic acid (MEAA) coated iron oxide NPs (MEAA-NPs) and TD/ZDS-coated iron oxide NPs (TD/ZDS-NPs) were performed. Interestingly, the $M_s$ of MEAA-NPs and TD/ZDS-NPs at room temperature were found to be ~63 and ~74 emu/g [Fe] (FIGS. 7b and 7c), respectively, which were close to the $M_s$ value of hydrophobic NPs. These results therefore suggest that the $M_s$ of as-synthesized SPIONs are largely insensitive to the heating, precipitation, sonication, and dialysis steps which were involved in the ligand exchange and purification processes. See, for example, Wu, W.; He, Q. G.; Jiang, C. Z. *Nanoscale Res. Lett.* 2008, 3, 397, which is incorporated by reference in its entirety. In addition, these results indicate that the TD/ZDS ligand coating is not likely to significantly change the magnetic behavior of as-synthesized SPIONs, which makes TD/ZDS a promising ligand coating for SPIONs used in potential MRI applications. See, for example, Kim, B. H.; Lee, N.; Kim, H.; An, K.; Park, Y. I.; Choi, Y.; Shin, K.; Lee, Y.; Kwon, S. G.; Na, H. B.; Park, J. G.; Ahn, T. Y.; Kim, Y. W.; Moon, W. K.; Choi, S. H.; Hyeon, T. *J. Am. Chem. Soc.* 2011, 133, 12624, Choi, J. S.; Lee, J. H.; Shin, T. H.; Song, H. T.; Kim, E. Y.; Cheon, J. *J. Am. Chem. Soc.* 2010, 132, 11015; Bruns, O. T.; Ittrich, H.; Peldschus, K.; Kaul, M. G.; Tromsdorf, U. I.; Lauterwasser, J.; Nikolic, M. S.; Mollwitz, B.; Merkell, M.; Bigall, N. C.; Sapra, S.; Reimer, R.; Hohenberg, H.; Weller, H.; Eychmuller, A.; Adam, G.; Beisiegel, U.; Heeren, *J. Nat. Nanotechnol.* 2009, 4, 193; and Freund, B.; Tromsdorf, U. I.; Bruns, O. T.; Heine, M.; Giemsa, A.; Bartelt, A.; Salmen, S. C.; Raabe, N.; Heeren, J.; Ittrich, H.; Reimer, R.; Hohenberg, H.; Schumacher, U.; Weller, H.; Nielsen, P. *ACS Nano* 2012, 6, 7318, each of which is incorporated by reference in its entirety.

Figure 8:
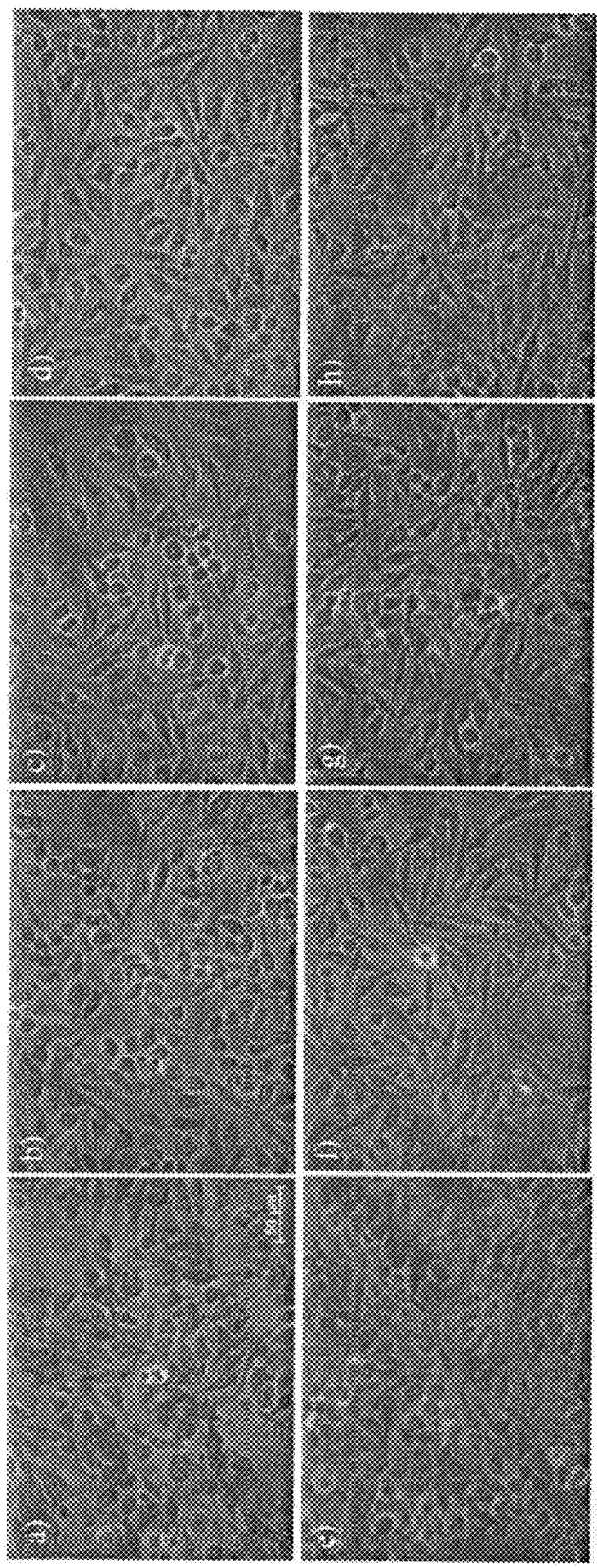
FIGS. 8a-8h are micrographs showing iron uptake into HeLa cells determined using Prussian blue after 24 hrs incubation: a) $FeCl_3$ (400 µg/mL), b) control, c) Dex-NPs (400 µg/mL), d) Dex-NPs (40 µg/mL), e) ZDS-NPs (400 µg/mL), ZDS-NPs (40 µg/mL), g) TD/ZDS-NPs (400 µg/mL), and h) TD/ZDS-NPs (40 µg/mL).

As ZDS-NPs and TD/ZDS-NPs are newly developed SPION systems, it is important to evaluate their non-specific uptake into cancer cells before they can potentially be used for specific targeting and imaging applications when functionalized by antibodies, peptides, or aptamers. See, for example, Gao, J. H.; Gu, H. W.; Xu, B. *Acc. Chem. Res.* 2009, 42, 1097; and Yoo, D.; Lee, J. H.; Shin, T. H.; Cheon, J. *Acc. Chem. Res.* 2011, 44, 863, each of which is incorporated by reference in its entirety. Therefore, the cellular uptake of ZDS-NPs and TD/ZDS-NPs into HeLa cells in a period of 24 hrs was investigated and compared the results with that of $FeCl_3$ and a well-established SPION system, i.e. dextran-coated iron oxide NPs (Dex-NPs). See, for example, Tassa, C.; Shaw, S. Y.; Weissleder, R. *Acc. Chem. Res.* 2011, 44, 842, which is incorporated by reference in its entirety. After iron staining by Prussian blue, FIG. 8a shows blue intracellular signal detected for HeLa cells incubated with 400 μg/mL $FeCl_3$, indicating intracellular Fe. In contrast, control HeLa cells that were not incubated with any iron source show minimal intracellular Fe (FIG. 8b). Similarly, HeLa cells incubated with Dex-NPs, ZDS-NPs, and TD/ZDS-NPs, also show minimal intracellular Fe (FIGS. 8c-h). The only exception is the blue ~20 μm spot in the middle of FIG. 8g, presumably caused by aggregation of cross-linked TD/ZDS-NPs, which have free thiol groups on their surface. See, for example, Liu, W. H.; Choi, H. S.; Zimmer, J. P.; Tanaka, E.; Frangioni, J. V.; Bawendi, M. *J. Am. Chem. Soc.* 2007, 129, 14530, which is incorporated by reference in its entirety. Generally, the non-specific cellular uptake of Dex-NPs, ZDS-NPs, or TD/ZDS-NPs was much less than that of $FeCl_3$. More importantly, although ZDS (MW: ~300 g/mol) and TD (MW: ~850 g/mol) ligands are relatively small compared to dextran (MW: ~6000 g/mol), no significant differences between Dex-NPs, ZDS-NPs, and TD/ZDS-NPs were found in terms of non-specific cellular uptake into HeLa cells. As Dex-NPs have served as a well-established SPION platform for molecular imaging, diagnostics, and therapeutics, ZDS-NPs and TD/ZDS-NPs with low non-specific cellular uptake also have the potential to be used for specific targeting and imaging studies. See, for example, Kelly, K. A.; Shaw, S. Y.; Nahrendorf, M.; Kristoff, K.; Aikawa, E.; Schreiber, S. L.; Clemons, P. A.; Weissleder, R. *Integr. Biol.* 2009, 1, 311; Gu, H. W.; Xu, K. M.; Xu, C. J.; Xu, B. *Chem. Commun.* 2006, 941; Ho, D. N.; Kohler, N.; Sigdel, A.; Kalluri, R.; Morgan, J. R.; Xu, C. J.; Sun, S. H. *Theranostics* 2012, 2, 66; and Karlsson, H. L.; Cronholm, P.; Gustafsson, J.; Moller, L. *Chem. Res. Toxicol.* 2008, 21, 1726, each of which is incorporated by reference in its entirety.

Figure 9:
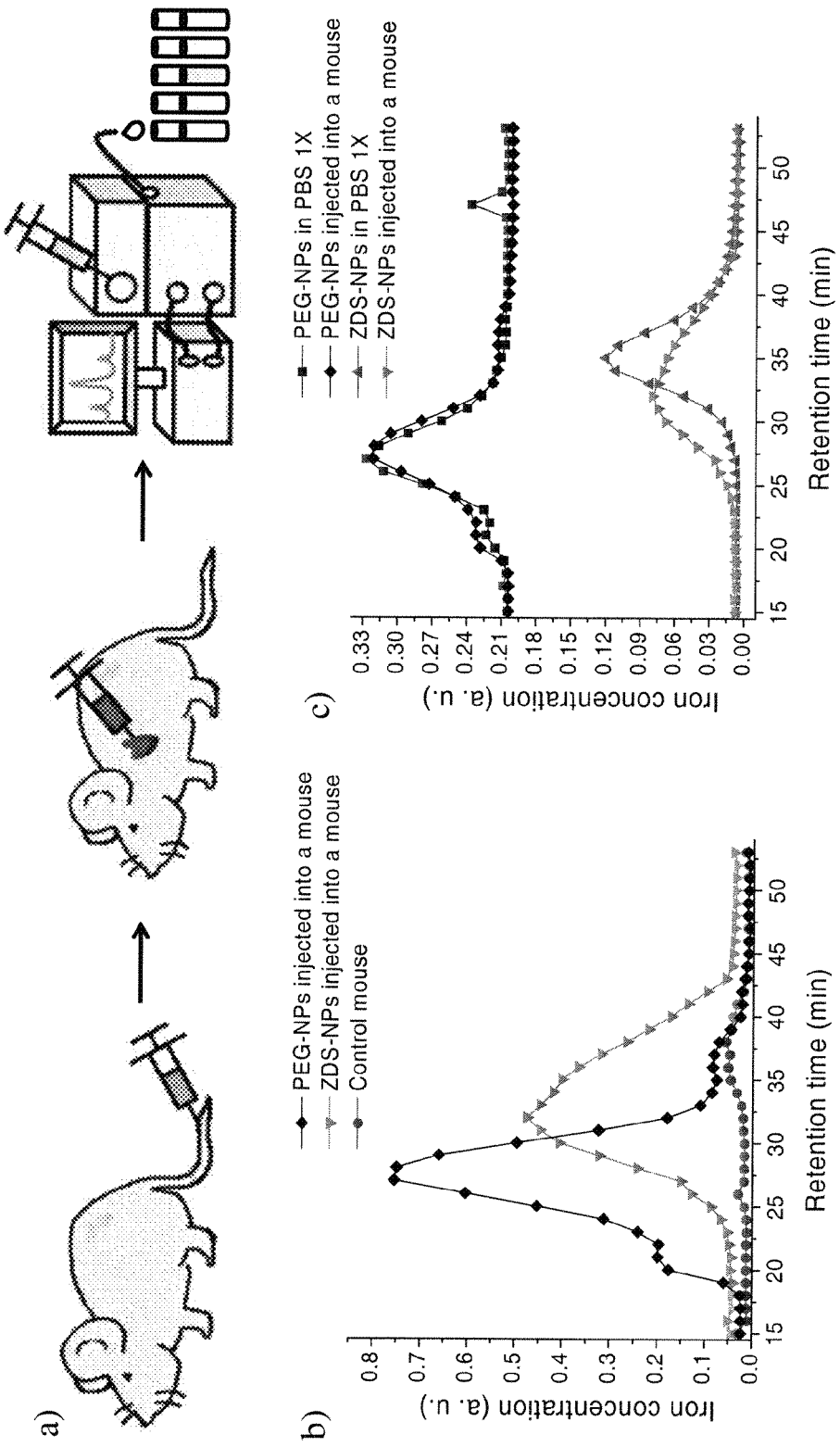
FIGS. 9a-c are drawings depicting a) Schematic of in vivo stability test (see Materials and Methods), b) in vivo stability chromatograms of NPs injected into mice, and c) in vivo stability chromatograms of NPs injected into mice and NPs in PBS 1× (data in panel b are included in panel c, while in panel b the data are not normalized and in panel c the data are normalized by area).

To further study the in vivo imaging potential of ZDS-NPs, an in vivo stability test was performed, which compared the sizes of NPs injected in mice to those incubated with PBS 1× (discussed above). Gel-filtration chromatography with a size-exclusion column was used, in which the retention times of NPs have an inverse relationship with the sizes of NPs (see, for example, Tromsdorf, U. I.; Bruns, O. T.; Salmen, S. C.; Beisiegel, U.; Weller, H. *Nano Lett.* 2009, 9, 4434, which is incorporated by reference in its entirety) to fractionize serum and/or NPs. Iron determination was then performed on each fraction using bathophenanthroline (BPT). The chromatograms of serum and/or NPs were then plotted as iron concentration (IC) versus retention time. The non-normalized data in FIG. 9b shows that the peak intensity of IC in serum from sample mice (injected with NPs) is about an order higher than that from the control mouse, indicating that BPT-based iron determination serves as a good method for analyzing the size distribution of NPs after incubation in vivo. After data normalization, FIG. 9c shows that in PBS 1× both iron oxide NPs encapsulated in PEG-lipid micelles (PEG-NPs, FIG. 9c, blue lines) and ZDS-NPs (FIG. 9c, pink lines) are nearly monodisperse with retention times of 27 and 35 min, respectively. The size of PEG-NPs injected in a mouse was almost the same as the size of PEG-NPs in PBS 1× (FIG. 9c, black lines), showing a nearly monodisperse distribution with a peak at 27 min. The size distribution of ZDS-NPs injected in a mouse slightly shifted to a new peak at 32 min (FIG. 9c, cyan lines), which is only a 3 min different from that of ZDS-NPs in PBS 1×, and corresponds to a size increase of ~4 nm in diameter. See, for example, Choi, H. S.; Liu, W.; Misra, P.; Tanaka, E.; Zimmer, J. P.; Ipe, B. I.; Bawendi, M. G.; Frangioni, J. V. *Nat. Biotechnol.* 2007, 25, 1165; and Wong, C.; Stylianopoulos, T.; Cui, J. A.; Martin, J.; Chauhan, V. P.; Jiang, W.; Popovic, Z.; Jain, R. K.; Bawendi, M. G.; Fukumura, D. *Proc. Natl. Acad. Sci. U.S.A.* 2011, 108, 2426, each of which is incorporated by reference in its entirety. As expected PEG-NPs show minimal non-specific affinity toward serum proteins. See, for example, Ai, H.; Flask, C.; Weinberg, B.; Shuai, X.; Pagel, M. D.; Farrell, D.; Duerk, J.; Gao, J. M. *Adv. Mater.* 2005, 17, 1949; Tong, S.; Hou, S. J.; Ren, B. B.; Zheng, Z. L.; Bao, G. *Nano Lett.* 2011, 11, 3720; or Mulder, W. J. M.; Strijkers, G. J.; Van Tilborg, G. A. F.; Cormode, D. P.; Fayad, Z. A.; Nicolay, K. *Acc. Chem. Res.* 2009, 42, 904, each of which is incorporated by reference in its entirety. These data also show that ZDS-NPs have low non-specific interactions with serum proteins in vivo and consequently that they are suitable for in vivo experiments, which is consistent with the in vitro results. The small size of ZDS ligands (MW: ~300 g/mol) compared to PEG-lipid ligands (MW: ~2800 g/mol) insures that ZDS-NPs have a significantly reduced size compared to PEG-NPs (FIG. 9c).

The magnetic behavior as well as tine in vitro and in vivo non-specific interactions of compact zwitterionic dopamine sulfonate (ZDS) ligand coated superparamagnetic iron oxide nanoparticles have been investigated. The TD and ZDS ligand did not change the superparamagnetism and $M_s$ (74 emu/g [Fe]) of hydrophobic NPs; moreover, ZDS-coated NPs had a small non-specific cellular uptake into HeLa cells after 24 hrs incubation, which is similar to dextran-coated NPs. In vivo stability tests showed low non-specific binding affinity for ZDS-coated NPs toward serum proteins and a smaller hydrodynamic size than NPs encapsulated in PEG-lipid micelles. These properties rendered ZDS-NPs and TD/ZDS-NPs suitable for in vitro and in vivo applications, where peptides, aptamers, or proteins could be conjugated for imaging and sensing, and when combined with an alternating magnetic field, the unaltered $M_s$ of ligand exchanged NPs (compared to hydrophobic NPs) could maximize the magneto-thermal effect of the as-synthesized hydrophobic NPs and thus enable ZDS-NPs and TD/ZDS-NPs to serve as a powerful sensitizer for hyperthermia treatment.

Other embodiments are within the scope of the following claims.

What is claimed is:

1. A water soluble nanoparticle comprising:
   an inorganic nanoparticle; and
   a ligand bound to a surface of the inorganic nanoparticle, wherein the ligand is of formula (II):

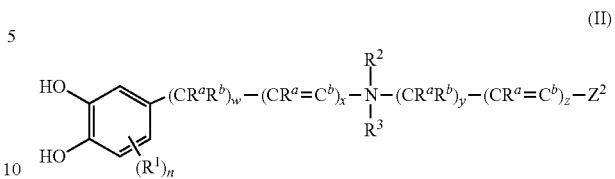

(II)

wherein $R^1$ is halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

n is 0, 1, 2, or 3;

each $R^a$ and each $R^b$, independently, is hydrogen, hydroxy, halo, alkyl, alkoxy, alkenyl, alkynyl, cycloalkyl, cycloalkoxy, cycloalkenyl, aryl, heteroaryl, heterocyclyl or $NH_2$; wherein each of alkyl, alkoxy, alkenyl, cycloalkyl, cycloalkoxy, cycloalkenyl, aryl, heteroaryl, and heterocyclyl are optionally substituted with 1 to 5 substituents independently selected from the group consisting of halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

each of w and y, independently, is 0 to 8; each of x and z, independently, is 0 to 4; provided that w and x are not simultaneously 0; and provided that y and z are not simultaneously 0;

$R^2$ is $R^c$; and $R^3$ is absent, or is $R^c$;

each $R^c$, independently, is hydrogen, alkyl, alkenyl, alkynyl, cycloalkyl, cycloalkenyl, aryl, heteroaryl, or heterocyclyl, wherein each of alkenyl, alkynyl, cycloalkyl, cycloalkenyl, aryl, heteroaryl, and heterocyclyl are optionally substituted with 1 to 5 substituents independently selected from the group consisting of halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl; and $Z^2$ is —OH, —SH, —$CO_2H$, —$OPO_3H_2$, —$PO_3H$, —$OSO_3H$, —$SO_3H$, or an ionized form thereof, wherein the inorganic nanoparticle includes a superparamagnetic iron oxide nanoparticle.

2. The nanoparticle of claim 1, wherein w is 2, 3, 4, 5, or 6;

x is zero;

$R^2$ and $R^3$ are each, independently, hydrogen or alkyl;

y is 2, 3, 4, 5, or 6; and z is 0.

3. The nanoparticle of claim 2, wherein $Z^2$ is —$SO_3H$, or an ionized form thereof.

4. The nanoparticle of claim 1, wherein the nanoparticle has a hydrodynamic diameter of 100 nm or less.

5. The nanoparticle of claim 1, wherein, for the ligand of formula (II),

A is

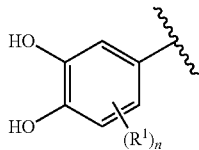

wherein $R^1$ is halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl, and n is 0, 1, 2, or 3;

$L^1$ is —$(CR^aR^b)_w$—$(CR^a\!=\!CR^b)_x$—, wherein w is 0 to 8, x is 0 to 4, provided that w and x are not simultaneously 0;

$L^2$ is —C(O)—, —C(O)$NR^c$—, —O—, —OC(O)—, —OC(O)O—, —OC(O)$NR^c$—, —$NR^c$—, —$NR^cC$(O)—, —$NR^cC$(O)O—, —$NR^cC$(O)$NR^c$—, or —S—;

H is —$[(CR^aR^b)_aO]_k$—$[(CR^aR^b)_bO]_l$—$[(CR^aR^b)_cO]_m$—, wherein each of a, b, and c, independently, is 2, 3, or 4, and each of k, l, and m, independently, is 0 to 100;

each $R^a$ and each $R^b$, independently, is hydrogen, hydroxy, halo, alkyl, alkoxy, alkenyl, alkynyl, cycloalkyl, cycloalkoxy, cycloalkenyl, aryl, heteroaryl, heterocyclyl or $NH_2$; wherein each of alkyl, alkoxy, alkenyl, cycloalkyl, cycloalkoxy, cycloalkenyl, aryl, heteroaryl, and heterocyclyl are optionally substituted with 1 to 5 substituents independently selected from the group consisting of halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

each $R^c$, independently, is hydrogen, alkyl, alkenyl, alkynyl, cycloalkyl, cycloalkenyl, aryl, heteroaryl, or heterocyclyl, wherein each of alkenyl, alkynyl, cycloalkyl, cycloalkenyl, aryl, heteroaryl, and heterocyclyl are optionally substituted with 1 to 5 substituents independently selected from the group consisting of halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl; and R' is $CO_2H$, —$NH_2$, —CH=$CH_2$, —C≡CH, —$N_3$, or —SH.

6. The nanoparticle of claim 1, wherein, for the ligand of formula (II),

A is

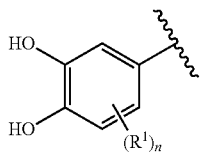

wherein $R^1$ is halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl, and n is 0, 1, 2, or 3;

$L^1$ is —$(CR^aR^b)_w$—$(CR^a\!=\!CR^b)_x$—, wherein w is 0 to 8, x is 0 to 4, provided that w and x are not simultaneously 0;

$L^2$ is —C(O)—, —C(O)$NR^c$—, —O—, —OC(O)—, —OC(O)O—, —OC(O)$NR^c$—, —$NR^c$—, —$NR^cC$(O)—, —$NR^cC$(O)O—, —$NR^cC$(O)$NR^c$—, or —S—;

H is —$[(CR^aR^b)_aO]_k$—$[(CR^aR^b)_bO]_l$—$[(CR^aR^b)_cO]_m$—, wherein each of a, b, and c, independently, is 2, 3, or 4, and each of k, l, and m, independently, is 0 to 100;

each $R^a$ and each $R^b$, independently, is hydrogen, hydroxy, halo, alkyl, alkoxy, alkenyl, alkynyl, cycloalkyl, cycloalkoxy, cycloalkenyl, aryl, heteroaryl, heterocyclyl or $NH_2$; wherein each of alkyl, alkoxy, alkenyl, cycloalkyl, cycloalkoxy, cycloalkenyl, aryl, heteroaryl, and heterocyclyl are optionally substituted with 1 to 5 substituents independently selected from the group consisting of halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

each $R^c$, independently, is hydrogen, alkyl, alkenyl, alkynyl, cycloalkyl, cycloalkenyl, aryl, heteroaryl, or heterocyclyl, wherein each of alkenyl, alkynyl, cycloalkyl, cycloalkenyl, aryl, heteroaryl, and heterocyclyl are optionally substituted with 1 to 5 substituents independently selected from the group consisting of halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl; and R is —C(O)NH—, —NHC(O)—, or —S—.

7. The nanoparticle of claim 6, wherein B is a dye or a member of a binding pair.

8. The nanoparticle of claim 7, further comprising a second, distinct ligand of formula (IV) bound to a surface of the inorganic nanoparticle.

9. A method of making a water-soluble nanoparticle, comprising:
providing an inorganic nanoparticle; and
contacting the inorganic nanoparticle with a ligand bound to a surface of the inorganic nanoparticle,
wherein the ligand is of formula (II):

(II)

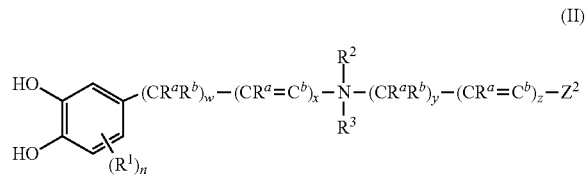

wherein
$R^1$ is halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;
n is 0, 1, 2, or 3;
each $R^a$ and each $R^b$, independently, is hydrogen, hydroxy, halo, alkyl, alkoxy, alkenyl, alkynyl, cycloalkyl, cycloalkoxy, cycloalkenyl, aryl, heteroaryl, heterocyclyl or $NH_2$; wherein each of alkyl, alkoxy, alkenyl, cycloalkyl, cycloalkoxy, cycloalkenyl, aryl, heteroaryl, and heterocyclyl are optionally substituted with 1 to 5 substituents independently selected from the group consisting of halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

each of w and y, independently, is 0 to 8; each of x and z, independently, is 0 to 4; provided that w and x are not simultaneously 0; and provided that y and z are not simultaneously 0;

$R^2$ is $R^c$; and $R^3$ is absent, or is $R^c$;

each $R^c$, independently, is hydrogen, alkyl, alkenyl, alkynyl, cycloalkyl, cycloalkenyl, aryl, heteroaryl, or heterocyclyl, wherein each of alkenyl, alkynyl, cycloalkyl, cycloalkenyl, aryl, heteroaryl, and heterocyclyl are optionally substituted with 1 to 5 substituents independently selected from the group consisting of halo, oxo, CN, OH, $NO_2$, alkyl, alkoxy, cycloalkoxy, cycloalkenoxy, amino, alkylamino, dialkylamino, acylamino, aminoacyl, alkylsulfonyl, alkylaminosulfonyl, and dialkylaminosulfonyl; and $Z^2$ is —OH, —SH, —$CO_2H$, —$OPO_3H_2$, —$PO_3H$, —$OSO_3H$, —$SO_3H$, or an ionized form thereof, wherein the inorganic nanoparticle includes a superparamagnetic iron oxide nanoparticle.

10. The method of claim 9, wherein w is 2, 3, 4, 5, or 6;

x is zero;

$R^2$ and $R^3$ are each, independently, hydrogen or alkyl;

y is 2, 3, 4, 5, or 6; and z is 0.

11. The method of claim 10, wherein $Z^2$ is —$SO_3H$, or an ionized form thereof.

* * * * *